(12) United States Patent
Flaherty et al.

(10) Patent No.: US 9,132,016 B2
(45) Date of Patent: Sep. 15, 2015

(54) IMPLANTABLE SHOULDER PROSTHESES

(75) Inventors: J. Christopher Flaherty, Auburndale, FL (US); Paul V. Fenton, Marblehead, MA (US); Amory Adrian Gregory Martin, Paris (FR)

(73) Assignee: Topsfield Medical GMBH (DE)

( * ) Notice: Subject to any disclaimer, the term of this patent is extended or adjusted under 35 U.S.C. 154(b) by 0 days.

(21) Appl. No.: 13/699,029

(22) PCT Filed: May 26, 2011

(86) PCT No.: PCT/US2011/038096
§ 371 (c)(1),
(2), (4) Date: Nov. 20, 2012

(87) PCT Pub. No.: WO2011/150180
PCT Pub. Date: Jan. 12, 2011

(65) Prior Publication Data
US 2013/0090737 A1    Apr. 11, 2013

Related U.S. Application Data

(60) Provisional application No. 61/348,465, filed on May 26, 2010.

(51) Int. Cl.
*A61F 2/40* (2006.01)
*A61F 2/46* (2006.01)
(Continued)

(52) U.S. Cl.
CPC .............. *A61F 2/40* (2013.01); *A61F 2/30749* (2013.01); *A61F 2/4014* (2013.01); *A61F 2/4081* (2013.01); *A61F 2/4612* (2013.01);
(Continued)

(58) Field of Classification Search
CPC . A61F 2/40; A61F 2/4081; A61F 2002/4085; A61F 2/30723; A61F 2002/3433; A61B 17/7098; A61M 2039/027
USPC .............................. 623/19.11–19.13; 606/300
See application file for complete search history.

(56) References Cited

U.S. PATENT DOCUMENTS 3,869,730 A   3/1975  Skobel
4,550,450 A  11/1985  Kinnett
(Continued)

FOREIGN PATENT DOCUMENTS

EP   1228739   8/2002
EP   1776935   4/2007
(Continued)

OTHER PUBLICATIONS

International Search Report dated Apr. 6, 2012, issued in corresponding International Application No. PCT/US2011/038096.
(Continued)

*Primary Examiner* — Bruce E Snow
*Assistant Examiner* — Brian Dukert
(74) *Attorney, Agent, or Firm* — Onello & Mello, LLP

(57) ABSTRACT

Prosthesis, tools and surgical methods treat joint instability by avoiding loosening over time. A shoulder prosthesis includes a humeral member with a humeral joint surface and a humeral fixation member and a glenoid member comprising a glenoid body with a glenoid joint surface, and a glenoid fixation member attaching the glenoid body to a scapula. The glenoid fixation member may be attached orthogonally to the scapula. A dampener may be included to absorb loads that may loosen one or more components of the prosthesis.

8 Claims, 30 Drawing Sheets

(51) Int. Cl.
*A61F 2/30* (2006.01)
*A61F 2/48* (2006.01)

(52) U.S. Cl.
CPC ......... *A61F2/30742* (2013.01); *A61F 2/30942* (2013.01); *A61F 2002/3007* (2013.01); *A61F 2002/30062* (2013.01); *A61F 2002/3067* (2013.01); *A61F 2002/30092* (2013.01); *A61F 2002/30433* (2013.01); *A61F 2002/30471* (2013.01); *A61F 2002/30563* (2013.01); *A61F 2002/30565* (2013.01); *A61F 2002/30578* (2013.01); *A61F 2002/30579* (2013.01); *A61F 2002/30635* (2013.01); *A61F 2002/30672* (2013.01); *A61F 2002/30736* (2013.01); *A61F 2002/30878* (2013.01); *A61F 2002/30884* (2013.01); *A61F 2002/4022* (2013.01); *A61F 2002/4085* (2013.01); *A61F 2002/4631* (2013.01); *A61F 2002/4666* (2013.01); *A61F 2002/484* (2013.01); *A61F 2310/00359* (2013.01)

(56) References Cited

U.S. PATENT DOCUMENTS

| | | | |
|---|---|---|---|
| D285,968 S | 9/1986 | Kinnett | |
| 4,986,833 A | 1/1991 | Worland | |
| 5,037,422 A | 8/1991 | Hayhurst et al. | |
| 5,080,673 A | 1/1992 | Burkhead et al. | |
| 5,108,440 A | 4/1992 | Grundei et al. | |
| 5,236,445 A | 8/1993 | Hayhurst et al. | |
| 5,356,413 A | 10/1994 | Martins et al. | |
| 5,437,677 A | 8/1995 | Shearer et al. | |
| 5,462,563 A | 10/1995 | Shearer et al. | |
| 5,489,310 A | 2/1996 | Mikhail | |
| 5,505,735 A | 4/1996 | Li | |
| 5,533,418 A | 7/1996 | Wu et al. | |
| 5,569,306 A | 10/1996 | Thal | |
| 5,584,835 A | 12/1996 | Greenfield | |
| 5,593,448 A | 1/1997 | Dong | |
| 5,634,926 A | 6/1997 | Jobe | |
| 5,643,321 A | 7/1997 | McDevitt | |
| 5,702,447 A | 12/1997 | Walch et al. | |
| 5,702,486 A | 12/1997 | Craig et al. | |
| 5,723,018 A | 3/1998 | Cyprien et al. | |
| 5,741,335 A | 4/1998 | Gerber et al. | |
| 5,782,866 A | 7/1998 | Wenstrom, Jr. | |
| 5,800,551 A | 9/1998 | Williamson et al. | |
| RE36,289 E | 8/1999 | Le et al. | |
| 6,022,373 A | 2/2000 | Li | |
| 6,045,582 A | 4/2000 | Prybyla | |
| 6,168,597 B1 * | 1/2001 | Biedermann et al. | 606/310 |
| 6,197,063 B1 | 3/2001 | Dews | |
| 6,200,330 B1 | 3/2001 | Benderev et al. | |
| 6,228,120 B1 | 5/2001 | Leonard et al. | |
| 6,241,732 B1 | 6/2001 | Overaker et al. | |
| 6,251,143 B1 | 6/2001 | Schwartz et al. | |
| 6,364,910 B1 | 4/2002 | Shultz et al. | |
| 6,371,958 B1 | 4/2002 | Overaker | |
| 6,379,386 B1 | 4/2002 | Resch et al. | |
| 6,436,144 B1 | 8/2002 | Ahrens | |
| 6,447,524 B1 | 9/2002 | Knodel et al. | |
| 6,458,136 B1 | 10/2002 | Allard et al. | |
| 6,620,197 B2 | 9/2003 | Maroney et al. | |
| 6,652,561 B2 | 11/2003 | Tran | |
| 6,660,008 B1 | 12/2003 | Foerster et al. | |
| 6,673,115 B2 | 1/2004 | Resch et al. | |
| 6,679,916 B1 | 1/2004 | Frankle et al. | |
| 6,699,289 B2 | 3/2004 | Iannotti et al. | |
| 6,783,549 B1 | 8/2004 | Stone et al. | |
| 6,790,234 B1 | 9/2004 | Frankle | |
| 6,875,234 B2 | 4/2005 | Lipman et al. | |
| 6,911,047 B2 | 6/2005 | Rockwood, Jr. et al. | |
| 6,932,834 B2 | 8/2005 | Lizardi et al. | |
| 6,932,841 B2 | 8/2005 | Sklar et al. | |
| 6,939,379 B2 | 9/2005 | Sklar | |
| 7,011,686 B2 | 3/2006 | Ball et al. | |
| 7,160,328 B2 | 1/2007 | Rockwood, Jr. et al. | |
| 7,175,663 B1 | 2/2007 | Stone | |
| 7,255,713 B2 * | 8/2007 | Malek | 623/17.12 |
| 7,329,284 B2 | 2/2008 | Maroney et al. | |
| 7,572,283 B1 | 8/2009 | Meridew | |
| 7,608,109 B2 | 10/2009 | Dalla Pria | |
| 7,717,947 B1 * | 5/2010 | Wilberg et al. | 606/304 |
| 7,794,484 B2 | 9/2010 | Stone et al. | |
| 8,105,385 B2 | 1/2012 | Maroney et al. | |
| 8,257,444 B2 | 9/2012 | Linares | |
| 8,673,015 B2 | 3/2014 | Maroney et al. | |
| 8,696,677 B2 | 4/2014 | Chavarria et al. | |
| 8,740,913 B2 | 6/2014 | Schneider | |
| 8,858,640 B2 | 10/2014 | Brunnarius et al. | |
| 2001/0011192 A1 * | 8/2001 | Ondrla et al. | 623/19.13 |
| 2001/0037153 A1 | 11/2001 | Rockwood, Jr. et al. | |
| 2002/0082702 A1 | 6/2002 | Resch et al. | |
| 2002/0099445 A1 | 7/2002 | Maroney et al. | |
| 2003/0195514 A1 | 10/2003 | Trieu et al. | |
| 2003/0199877 A1 | 10/2003 | Steiger et al. | |
| 2004/0034431 A1 | 2/2004 | Maroney et al. | |
| 2004/0064189 A1 | 4/2004 | Maroney et al. | |
| 2004/0122519 A1 | 6/2004 | Wiley et al. | |
| 2004/0220674 A1 | 11/2004 | Pria | |
| 2004/0230197 A1 | 11/2004 | Tornier et al. | |
| 2005/0060039 A1 | 3/2005 | Cyprien | |
| 2005/0209700 A1 | 9/2005 | Rockwood, Jr. et al. | |
| 2005/0267480 A1 | 12/2005 | Suddaby | |
| 2006/0020344 A1 | 1/2006 | Shultz et al. | |
| 2006/0074421 A1 | 4/2006 | Bickley et al. | |
| 2006/0122705 A1 | 6/2006 | Morgan | |
| 2006/0276903 A1 | 12/2006 | Maroney et al. | |
| 2007/0055380 A1 | 3/2007 | Berelsman et al. | |
| 2007/0078519 A1 | 4/2007 | Klotz | |
| 2007/0100458 A1 | 5/2007 | Dalla Pria | |
| 2007/0118227 A1 | 5/2007 | King et al. | |
| 2007/0179624 A1 * | 8/2007 | Stone et al. | 623/19.13 |
| 2007/0198094 A1 | 8/2007 | Berelsman et al. | |
| 2007/0219637 A1 | 9/2007 | Berelsman et al. | |
| 2007/0219638 A1 | 9/2007 | Jones et al. | |
| 2008/0109000 A1 | 5/2008 | Maroney et al. | |
| 2008/0177393 A1 | 7/2008 | Grant et al. | |
| 2010/0070044 A1 | 3/2010 | Maroney et al. | |
| 2010/0228352 A1 | 9/2010 | Courtney, Jr. et al. | |
| 2010/0241235 A1 | 9/2010 | Basamania et al. | |
| 2010/0274359 A1 | 10/2010 | Brunnarius et al. | |
| 2011/0060373 A1 * | 3/2011 | Russell et al. | 606/304 |
| 2013/0261754 A1 | 10/2013 | Anthony et al. | |
| 2014/0005789 A1 | 1/2014 | Chavarria et al. | |
| 2014/0039632 A1 | 2/2014 | Hollis | |
| 2014/0142711 A1 | 5/2014 | Maroney et al. | |
| 2014/0350611 A1 | 11/2014 | Baird et al. | |
| 2015/0032214 A1 | 1/2015 | Brunnarius et al. | |

FOREIGN PATENT DOCUMENTS

| | | |
|---|---|---|
| EP | 1782764 | 5/2007 |
| EP | 2229922 | 9/2010 |
| EP | 2243444 | 10/2010 |
| FR | 2937245 | 4/2010 |

OTHER PUBLICATIONS

European search report dated Dec. 18, 2014 issued in corresponding European application No. 12758053.8-1654/2685940.
Frederick A. Matsen III, M.D., Ream and Run Non-Prosthetic Glenoid Arthroplasty for Shoulder Arthritis:Regenerative Cementless Surgery Designed for Individuals Desiring Higher Levels of Activity Than Recommended for Traditional Total Joint Replacement, Oct. 17, 2006 pp. 1-13, University of Washington, Seattle.

* cited by examiner

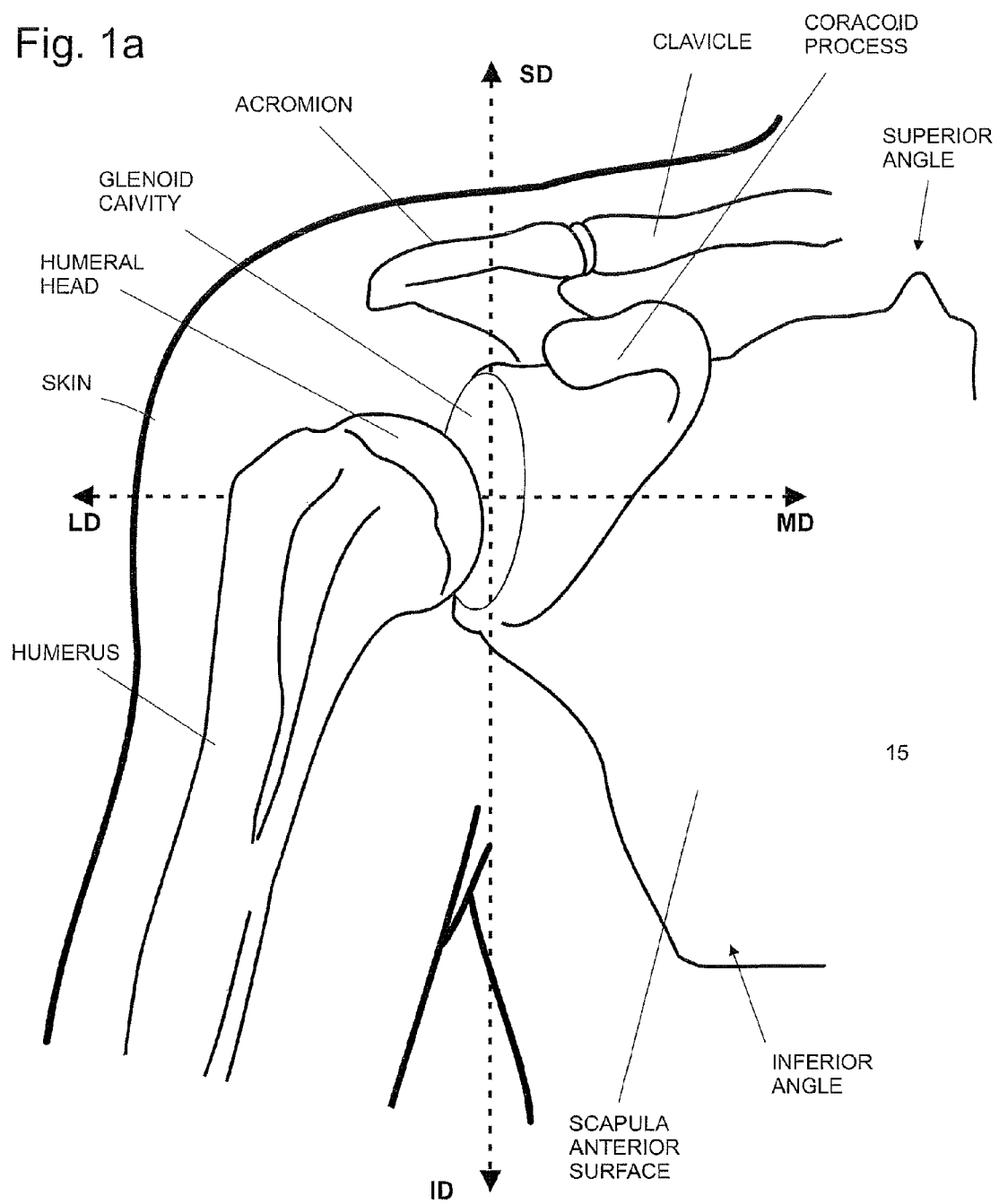

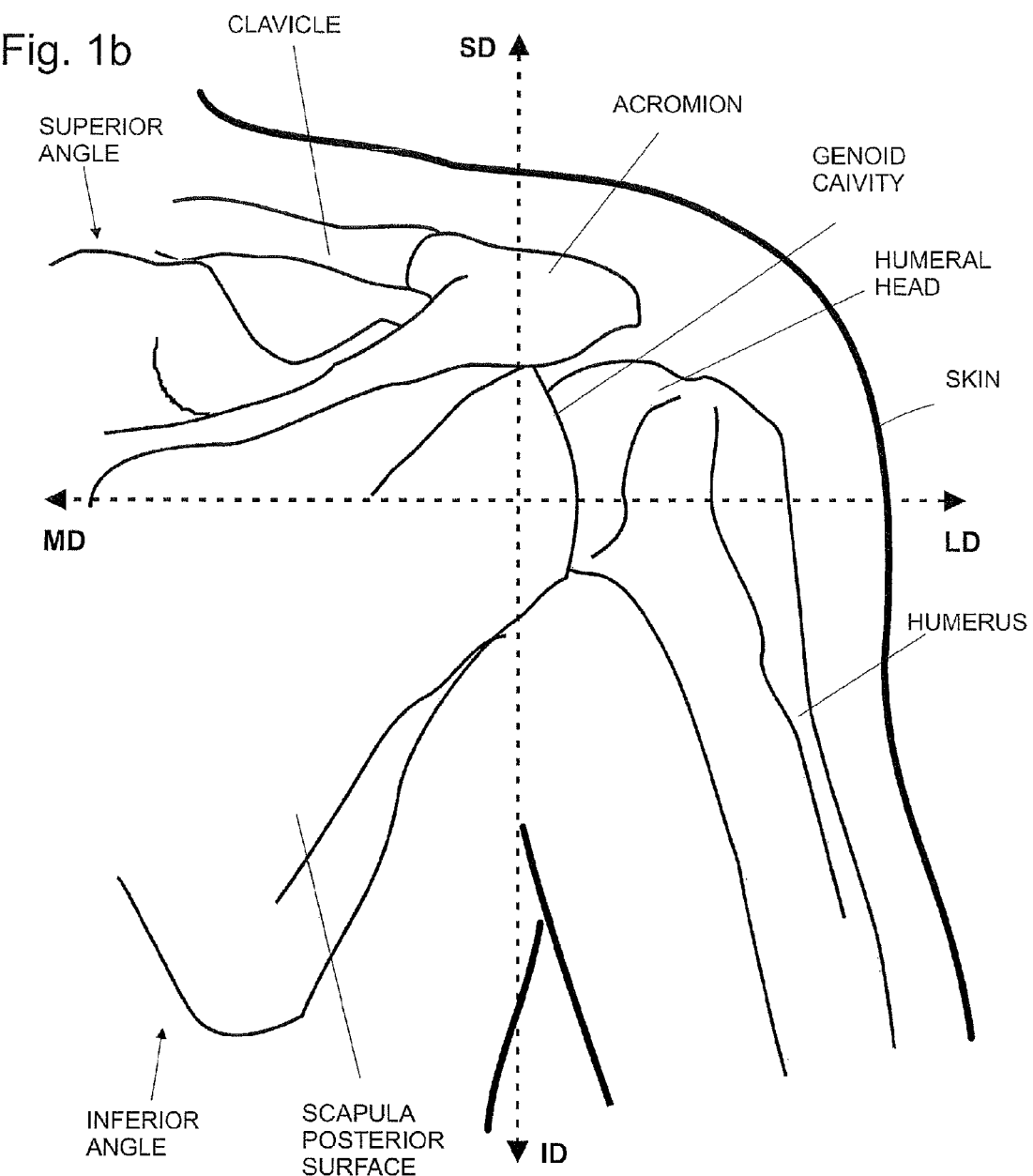

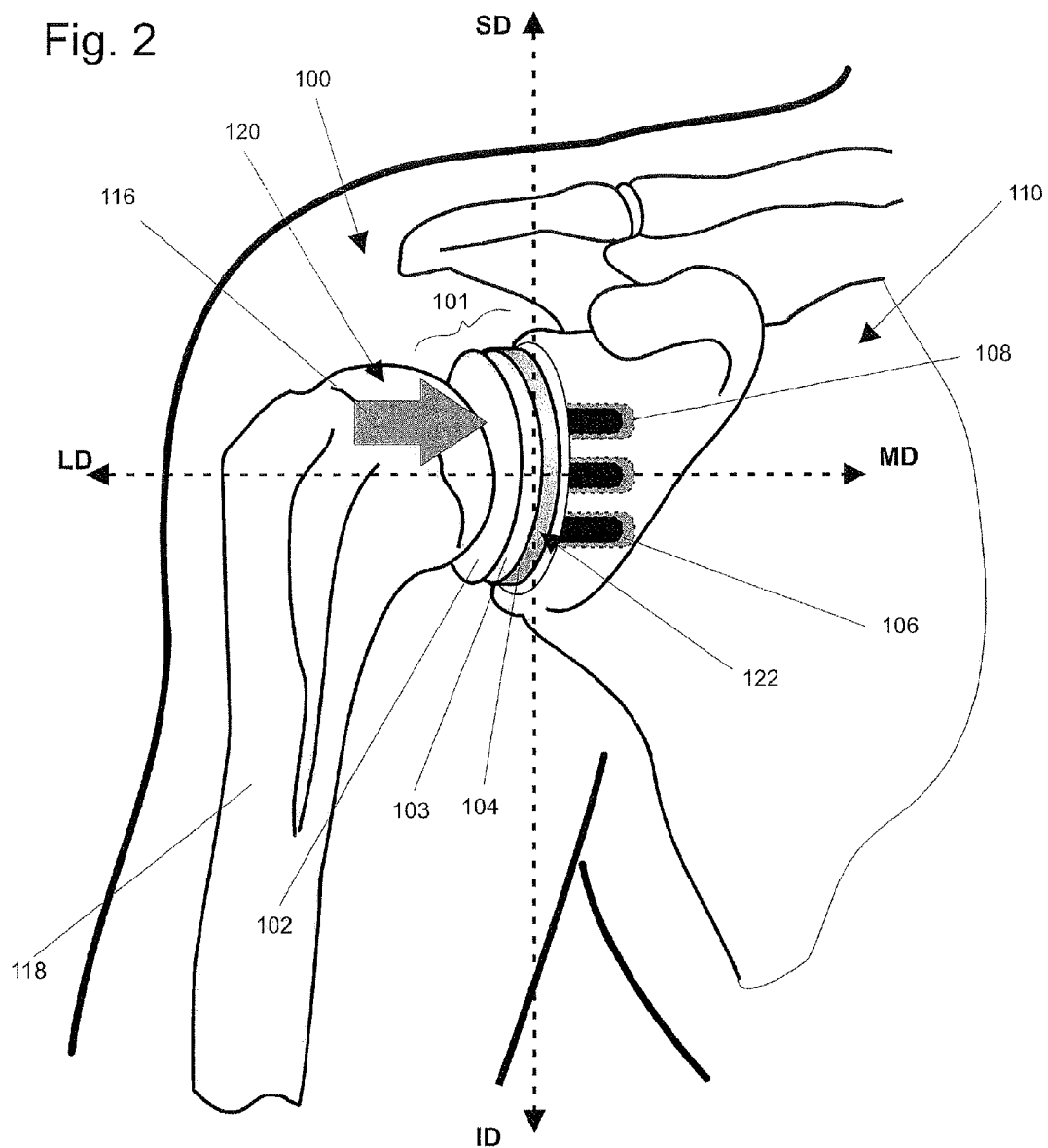

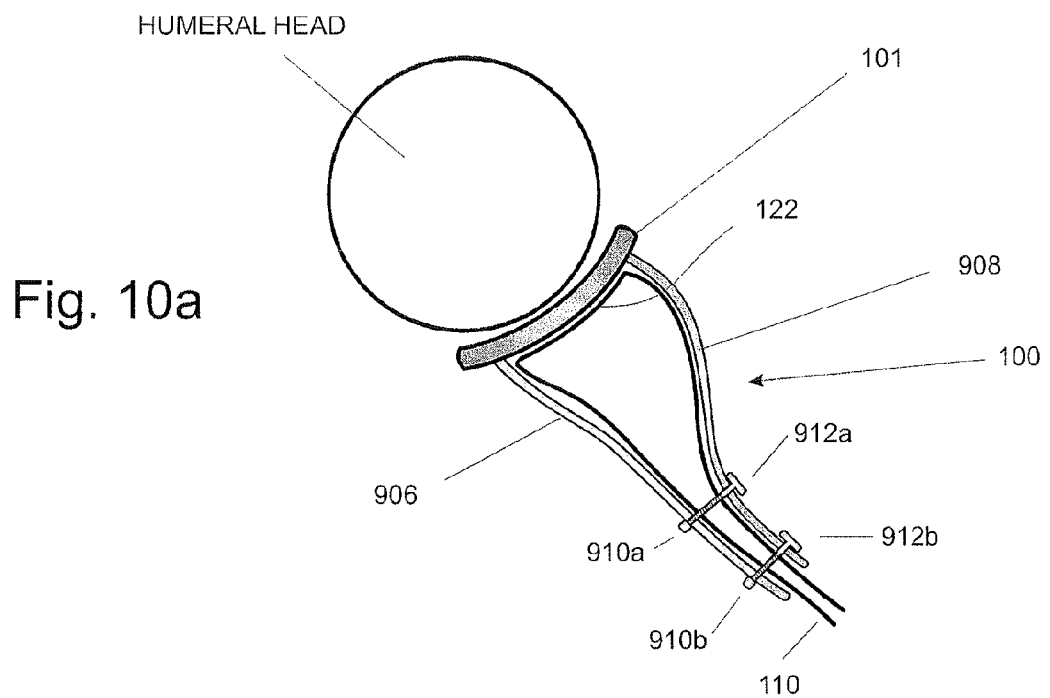
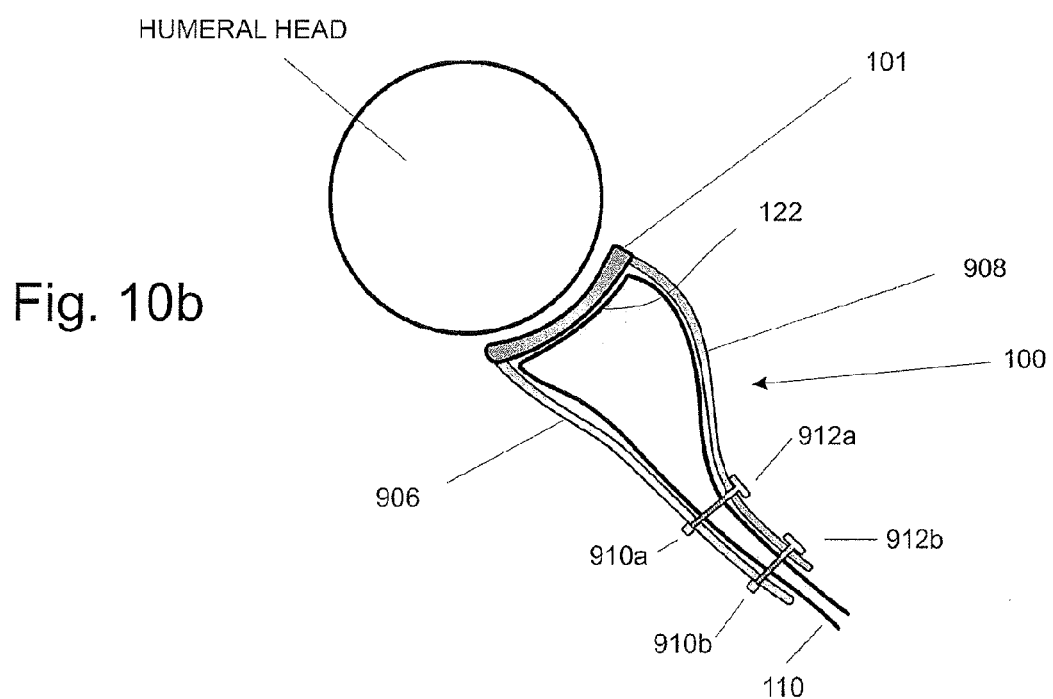

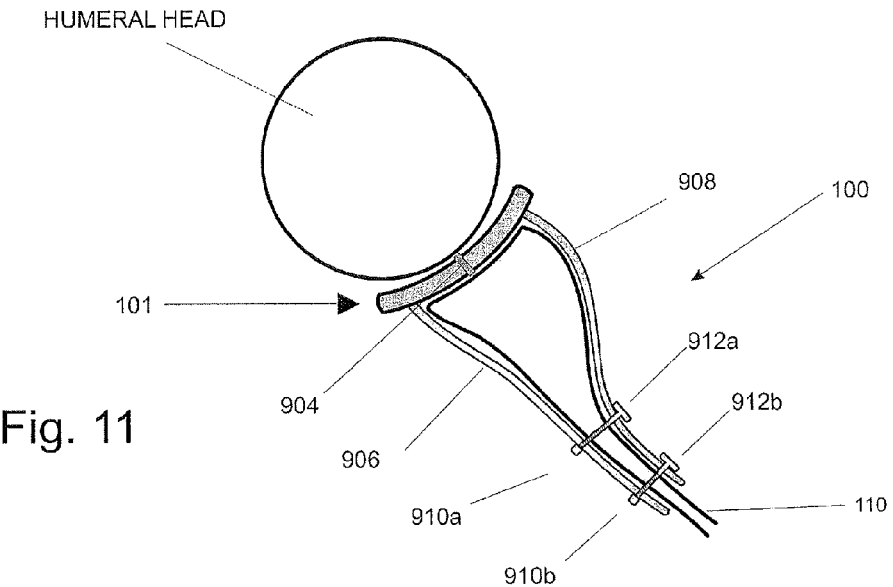
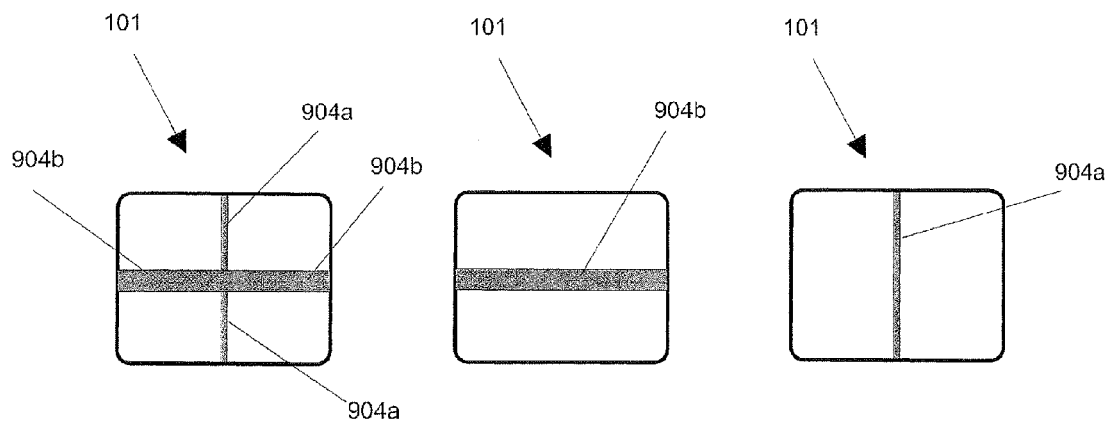
Fig. 12a  Fig. 12b  Fig. 12c

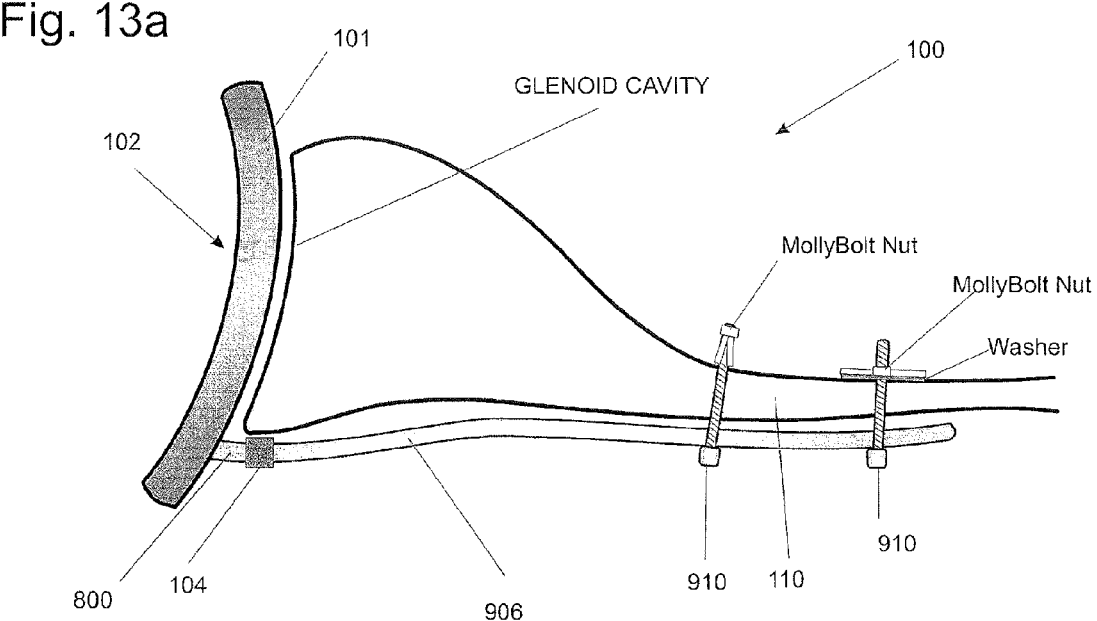
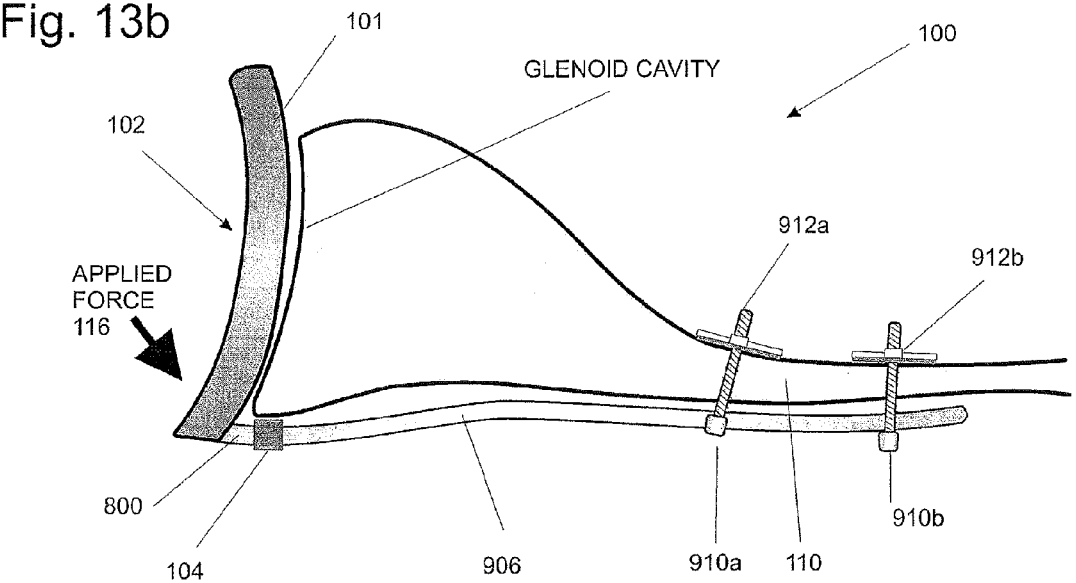

IMPLANTABLE SHOULDER PROSTHESES

RELATED APPLICATION

The present application claims the benefit of U.S. Ser. No. 61/348,465, filed May 26, 2010, the content of which is incorporated herein by reference in its entirety.

FIELD OF THE APPLICATION

Embodiments of the present application relate generally to implantable prostheses, and more particularly, to implantable shoulder prostheses, methods of implanting shoulder prostheses and surgical tools for implanting shoulder prostheses.

BACKGROUND

Many joints of the human body naturally articulate relative to one another. Generally, the articulation surfaces of these joints are substantially smooth and without abrasion. However, joints, such as shoulder joints, undergo degenerative changes due to a variety of causes, such as, disease, injury, exercise and other strenuous activities, and various other issues. When these degenerative changes become advanced, to the point of becoming irreversible, such joints or portions thereof may need to be replaced with one or more prosthetics.

In light of the degenerative changes found in shoulder joints, various shoulder prosthetics of conventional design have been proposed. However, conventional shoulder prosthetics and their associated surgical components suffer from many disadvantages. For example, glenoid components of conventional design are subject to various types of load forces, such as, shear forces, anterior/posterior forces, lateral/medial forces, and rotational forces, which may cause notching and chipping of bone and/or loosening of the implanted components, thereby reducing the lifespan of the prosthetic. In addition, such load forces may create a rocking moment causing glenoid components to cantilever, which can further result in notching and chipping of bone and/or separation of the glenoid component from the scapula. Furthermore, the loosening of conventional shoulder prosthetics may pulverize, grind, crush and deform portions of a scapula, for example, a glenoid cavity of a scapula, which as a result, can prohibit the replacement of a worn, damaged or non-functional shoulder prosthetic. For these and other reasons, there is a need for improved shoulder prosthetics.

SUMMARY

Embodiments of the present application are directed toward implantable shoulder prostheses, methods of implanting shoulder prostheses and surgical tools for implanting shoulder prostheses that further address and reduce notching and chipping of bone and component loosening associated with implantable shoulder prostheses. In particular, embodiments provide implantable shoulder prostheses and methods of implantation that realize, among other features, a dampening characteristic that reduces an applied load force through the absorption and dissipation of said force. Further embodiments provide, among other features, multiple fixation members for attaching implantable shoulder prosthesis and capabilities for attaching implantable shoulder prostheses to multiple surfaces of a scapula. Still further embodiments provide methods of manufacturing shoulder prosthesis including obtaining an image of a patient, such as an image including the contours of a patient's scapula, and manufacturing fixation members based on these contours. Although embodiments may be described with reference to shoulder prosthesis, joint components and methods for implantation described herein are applicable to other joints, such as hips, knees, elbows, wrists, digits and other joints. Patients applicable to these prosthetics include humans and other mammals, as well as other animalia.

In one aspect an implantable shoulder prosthesis comprises: a humeral member comprising: a humeral body comprising a humeral joint surface; and at least one humeral fixation member constructed and arranged to attach the humeral body to a humeral bone; a glenoid member comprising: a glenoid body comprising a glenoid joint surface; and at least one glenoid fixation member constructed and arranged to attach the glenoid body to a scapula; and a dampener; wherein the humeral joint surface and the glenoid joint surface are constructed and arranged to rotatably interface; and wherein the dampener is constructed and arranged to absorb a load force transferred to the at least one glenoid fixation member.

In some embodiments the implantable shoulder prosthesis is constructed and arranged to be implanted in a two legged mammal.

In some embodiments the humeral member comprises at least a portion of the dampener.

In some embodiments the dampener comprises a first portion and a second portion.

In some embodiments the at least one glenoid fixation member comprises the dampener second portion.

In some embodiments the humeral joint surface surrounds the glenoid joint surface such that movement of the humeral bone is at least partially constrained in two directions.

In some embodiments the humeral joint surface is rotatably connected to the glenoid joint surface such that the movement of the humeral bone is fully constrained in one direction and at least partially constrained along two axes.

In some embodiments the at least one humeral fixation member comprises a projecting stem.

In some embodiments the at least one humeral fixation member comprises a threaded projection.

In some embodiments the at least one humeral fixation member comprises a finned projection.

In some embodiments the at least one humeral fixation member is constructed and arranged to be secured within a humeral bone In some embodiments the glenoid member comprises the dampener.

In some embodiments the dampener comprises a first portion and a second portion.

In some embodiments the humeral member comprises the dampener second portion.

In some embodiments the glenoid joint surface surrounds the humeral joint surface such that movement of the humeral bone is at least partially constrained in two directions.

In some embodiments the glenoid joint surface is concave.

In some embodiments the humeral joint surface is convex.

In some embodiments the glenoid joint surface is convex.

In some embodiments the humeral joint surface is concave.

In some embodiments the at least one glenoid fixation member extends into the scapula in a medial direction.

In some embodiments the at least one glenoid fixation member comprises at least one rigid portion.

In some embodiments the at least one glenoid fixation member comprises at least one flexible portion.

In some embodiments the at least one glenoid fixation member comprises at least one rigid portion and at least one flexible portion.

In some embodiments the at least one glenoid fixation member is selected from the group consisting of: a fin, a pin, a peg and a screw.

In some embodiments the at least one glenoid fixation member extends medially along one or more of: the anterior surface of the scapula and the posterior surface of the scapula.

In some embodiments the at least one glenoid fixation member comprises at least one attachment orifice.

In some embodiments at least one attachment device constructed and arranged to pass through the attachment orifice and into the scapula.

In some embodiments the at least one attachment device is selected from the group consisting of: a screw; a pin, a peg; a fin; and combinations thereof.

In some embodiments at least one attachment mechanism, the at least one attachment mechanism constructed and arranged to secure the at least one glenoid fixation member to the scapula.

In some embodiments the at least one attachment mechanism comprises a bone screw.

In some embodiments the at least one attachment mechanism comprises a molly bolt.

In some embodiments the at least one attachment mechanism comprises an attachment device selected from the group consisting of: a screw; a machine screw; a nut; a lock nut; a rivet; a bolt; a washer; and combinations thereof.

In some embodiments the dampener is positioned between the glenoid joint surface and the scapula.

In some embodiments the dampener is positioned between the at least one glenoid fixation member and the scapula.

In some embodiments the at least one glenoid fixation member comprises one or more of a pin, a peg, a screw and a fin, and wherein the dampener surrounds the at least one glenoid fixation member.

In some embodiments the dampener is positioned between the glenoid joint surface and the glenoid fixation member.

In some embodiments the glenoid member comprises a rigid section, and the dampener is positioned between the glenoid joint surface and the rigid section.

In some embodiments the at least one glenoid fixation member comprises at least two glenoid fixation members and the dampener is positioned between the glenoid joint surface and the at least two glenoid fixation members.

In some embodiments the at least one glenoid fixation member comprises a first rigid portion and a second rigid portion, and wherein the dampener is positioned between the first rigid portion and the second rigid portion.

In some embodiments the dampener is positioned between the humeral joint surface and the at least one humeral fixation member.

In some embodiments the dampener is positioned between the at least one humeral fixation member and the humeral bone.

In some embodiments the dampener surrounds at least a portion of the humeral fixation member.

In some embodiments the at least one humeral fixation member comprises a first rigid portion and a second rigid portion, wherein the dampener is positioned between the first rigid portion and the second rigid portion.

In some embodiments the dampener comprises a compressible material.

In some embodiments the dampener comprises a compressible assembly.

In some embodiments the compressible assembly comprises a pneumatic or hydraulic assembly.

In some embodiments the compressible assembly comprises a fluid filled reservoir.

In some embodiments the dampener comprises a spring.

In some embodiments the spring is selected from the group of springs consisting of: torsional, compression, constant force, Belleville, and combinations thereof.

In some embodiments the dampener comprises bone bonding material.

In some embodiments the bond bonding material is constructed and arranged to secure the humeral member to the humeral bone.

In some embodiments the bone bonding material surrounds at least a portion of the at least one humeral fixation member.

In some embodiments the bone bonding material secures the glenoid member to the glenoid cavity of the scapula.

In some embodiments the bone bonding material surrounds at least a portion of the at least one glenoid fixation member.

In some embodiments the bone bonding material comprises elastomeric material.

In some embodiments the bone bonding material comprises flexible bone cement.

In some embodiments the dampener comprises fill material.

In some embodiments the fill material is positioned in a space previously occupied by bone tissue.

In some embodiments the fill material comprises bone cement.

In some embodiments the fill material comprises flexible adhesive.

In some embodiments the flexible adhesive comprises elastomeric adhesive.

In some embodiments the dampener is further constructed and arranged to absorb a load force transferred to the at least one humeral fixation member.

In some embodiments the load comprises a compressive load.

In some embodiments the load comprises a torsional load.

In some embodiments the load comprises a relatively continuous load.

In some embodiments the load comprises a dynamic load.

In some embodiments the dampener comprises a first dampening portion and a second dampening portion.

In some embodiments the glenoid member comprises the first dampening portion and the humeral member comprises the second dampening portion.

In some embodiments the at least one glenoid fixation member comprises a first glenoid fixation member and a second glenoid fixation member and wherein the first dampening portion absorbs a load transferred to the first glenoid fixation member, and the second dampening portion absorbs a load transferred to the second glenoid fixation member.

In some embodiments the first dampening portion has a compression ratio greater than a compression ratio of the second dampening portion.

In some embodiments first dampening portion has a compression ratio equal to a compression ratio of the second dampening portion.

In some embodiments the first dampening portion is constructed and arranged to absorb a force applied in a first direction and the second dampening portion is constructed and arranged to absorb or reduce a force applied in a second direction.

In some embodiments the first direction and the second direction are different.

In another aspect an implantable shoulder prosthesis comprises: a glenoid member comprising: a glenoid body comprising a glenoid joint surface constructed and arranged to provide a bearing surface for a head portion of a humerus; a first glenoid fixation member constructed and arranged to attach the glenoid member to a scapula; and a second glenoid fixation member comprising an engageable attachment element constructed and arranged to further attach the glenoid member to the scapula; wherein said second glenoid fixation member attachment element is constructed and arranged to be engaged at least twenty fours hours after implantation of the shoulder prosthesis.

In some embodiments the implantable shoulder prosthesis is constructed and arranged to be implanted in a two legged mammal.

In some embodiments the first glenoid fixation member is constructed and arranged to be engaged in a first internal portion of the scapula.

In some embodiments the second glenoid fixation member is constructed and arranged to be engaged in a second internal portion of the scapula.

In some embodiments the first glenoid fixation member is constructed and arranged to be engaged with the glenoid cavity of the scapula.

In some embodiments the second glenoid fixation member is constructed and arranged to be engaged with the glenoid cavity of the scapula.

In some embodiments the second glenoid fixation member is constructed and arranged to be engaged with one or more of: the anterior surface of the scapula and the posterior surface of the scapula.

In some embodiments the first glenoid fixation member is constructed and arranged to be engaged with one or more of: the anterior surface of the scapula and the posterior surface of the scapula.

In some embodiments the second glenoid fixation member is constructed and arranged to be engaged with the glenoid cavity of the scapula.

In some embodiments the second glenoid fixation member is constructed and arranged to be engaged with one or more of: the anterior surface of the scapula and the posterior surface of the scapula.

In some embodiments the first glenoid fixation member comprises the second glenoid fixation member.

In some embodiments the attachment element comprises an expandable member constructed and arranged to expand into bone.

In some embodiments the attachment element comprises an expandable member constructed and arranged to expand at least a portion of the first glenoid fixation member into bone.

In some embodiments the attachment element comprises an extendable member constructed and arranged to extend into bone.

In some embodiments the attachment element is positioned proximate the first glenoid fixation member.

In some embodiments the attachment element comprises an expandable member constructed and arranged to expand into bone.

In some embodiments the attachment element comprises an expandable member constructed and arranged to expand at least a portion of the first glenoid fixation member into bone.

In some embodiments the attachment element comprises an extendable member constructed and arranged to extend into bone.

In some embodiments the attachment element is positioned within the first glenoid fixation member.

In some embodiments the attachment element comprises an expandable member constructed and arranged to expand at least a portion of the first glenoid fixation member.

In some embodiments the attachment element comprises an extendable member constructed and arranged to extend beyond the first glenoid fixation member and into bone.

In some embodiments the attachment element is an attachment device selected from the group consisting of: a fin; a pin; a peg; a screw; and combinations thereof.

In some embodiments the attachment element is constructed and arranged to rotate to attach the glenoid member to the scapula.

In some embodiments the attachment element is selected from the group consisting of: a pin, a peg, a screw, a fin and combinations thereof.

In some embodiments the attachment element comprises a sharpened distal end.

In some embodiments the attachment element comprises a proximal end constructed and arranged to removably engage with a tool.

In some embodiments said proximal end comprises one or more of a hexagonal shaped cavity, a slot, or two slots positioned approximately ninety degrees from each other.

In some embodiments the attachment element comprises an expandable portion.

In some embodiments an expansion tool construct and arranged to operably expand said expandable portion.

In some embodiments the expansion tool comprises an expandable balloon or an expandable cage.

In some embodiments the attachment element comprises a shape modifiable portion constructed and arranged to change shape to further attach the glenoid member to the scapula.

In some embodiments the shape modifiable portion comprises a least a plastically deformable material.

In some embodiments the shape modifiable portion comprises at least a shaped memory material.

In some embodiments the shape modifiable portion further comprises at least a plastically deformable material, and wherein the shaped memory material is constructed and arranged to deform the plastically deformable material at least twenty four hours after implantation of the shoulder prosthesis.

In some embodiments the attachment element is constructed and arranged to further attach the glenoid member to the scapula in the presence of a magnetic field.

In some embodiments the attachment element is constructed and arranged to further attach the glenoid member to the scapula in the presence of a temperature above body temperature.

In some embodiments the attachment element is constructed and arranged to automatically further attach the glenoid member to the scapula.

In some embodiments the attachment element is constructed and arranged to continuously further attach the glenoid member to the scapula.

In some embodiments the attachment element is constructed and arranged to further attach the glenoid member to the scapula based on a condition of the patient receiving the shoulder prosthesis.

In some embodiments the patient condition is loosening of the glenoid member.

In some embodiments the patient condition is the presence of a void in a bone of the patient.

In some embodiments the patient condition is suspected presence of a void in a bone of the patient.

In some embodiments the attachment element is biased with a constant force.

In some embodiments the implantable shoulder prosthesis further comprises an access port constructed and arranged for a tool to pass therethrough, In some embodiments the access port is constructed and arranged to be accessed percutaneously.

In some embodiments the access port is constructed and arranged to be accessed in a minimally invasive procedure.

In some embodiments the access port is constructed and arranged to be accessed in an open surgical procedure.

In some embodiments the access port provides access to a portion of the first glenoid fixation member.

In some embodiments the access port provides access to a portion of the second glenoid fixation member.

In some embodiments the access port provides access to the attachment element.

In some embodiments the access port comprises a mechanical valve.

In some embodiments the mechanical valve is constructed and arranged to removably engage with the tool.

In some embodiments the access port comprises a resealable septum.

In some embodiments the septum is constructed and arranged to be penetrated by the tool avoiding removal of septum material.

In some embodiments the access port prevents biological or other contamination from passing through said access port.

In some embodiments the access port further comprises a transport tube wherein the tool can inject material through said transport tube.

In some embodiments the transport tube is constructed and arranged to have material delivered to a location between the glenoid member and the scapula.

In some embodiments the transport tube is constructed and arranged to have material delivered to a location selected from the group consisting of: within the glenoid member; proximate the glenoid member; and combinations thereof.

In some embodiments the transport tube is constructed and arranged to have material delivered to one or more of the first glenoid fixation member; the second glenoid fixation member; and the attachment element.

In some embodiments the material is selected from the group consisting of: adhesive; cement; saline; an agent such as a drug; and combinations thereof.

In some embodiments the material is fill material.

In some embodiments the fill material is constructed and arranged to expand at least a port of the glenoid member.

In some embodiments the fill material is constructed and arranged to expand the attachment element.

In some embodiments the fill material is constructed and arranged to fill a void in a bone.

In some embodiments the material is below body temperature.

In some embodiments the material is above body temperature.

In some embodiments the fill material transport tube of the resealable septum provides an access port through which fill material can be injected.

In some embodiments the implantable shoulder prosthesis further comprises an access port constructed and arranged for a tool to pass therethrough, In some embodiments the access port comprises a resealable septum.

In some embodiments the access port comprises a mechanical valve.

In some embodiments the access port is constructed and arranged to be accessed percutaneously.

In some embodiments the fill material comprises a material selected from the group consisting of: adhesive, cement; and combinations thereof.

In some embodiments the fill material is flexible.

In some embodiments the fill material is rigid.

In some embodiments the tool comprises fill material constructed and arranged to fill a void in bone.

In some embodiments the first glenoid portion or the second glenoid portion comprise an expandable member and the fill material is constructed and arranged to expand the expandable member into bone.

In some embodiments the fill material is selected from the group consisting of: adhesive, cement, water, saline, antibiotics, and combinations thereof.

In some embodiments a tool.

In some embodiments the tool comprises a sharpened tip.

In some embodiments the tip is a needle tip.

In some embodiments the tip is a screwdriver tip.

In some embodiments the tool is constructed and arranged to inject material into or proximate the glenoid member.

In some embodiments said injected material is constructed and arranged to fill a space.

In some embodiments the space is space previously occupied by bone.

In some embodiments the injected material is selected form the group consisting of: adhesive; cement; saline; an agent such as a drug; and combinations thereof.

In some embodiments the material is delivered above body temperature.

In some embodiments the material is delivered below body temperature.

In some embodiments the tool is constructed and arranged to engage the attachment element.

In some embodiments the tool is further constructed and arranged to expand the attachment element.

In some embodiments the tool is further constructed and arranged to modify the shape of the attachment element.

In some embodiments the tool is further constructed and arranged to deliver energy to the attachment element.

In some embodiments the energy is selected from the group consisting of: magnetic energy; thermal energy; and combinations thereof.

In some embodiments the tool comprises a screwdriver.

In some embodiments the tool comprises a tip selected from the group consisting of: hex head; slotted head; Phillips head; and torque head.

In some embodiments the tip is sharp.

In some embodiments of the inventive concepts are directed to a method of implanting a shoulder prosthesis configured in accordance with embodiments described herein.

In another aspect an implantable shoulder prosthesis comprises: a glenoid member comprising: a glenoid joint surface that is constructed and arranged to provide a bearing surface for a head portion of a humerus; and a glenoid fixation member constructed and arranged to attach a scapula; a pressure sensing system configured to measure a pressure between the glenoid member and the scapula.

In some embodiments the scapula is within a two legged mammal.

In some embodiments a dampener.

In some embodiments the glenoid joint surface is concave.

In some embodiments the glenoid joint surface is convex.

In some embodiments the pressure sensing assembly comprises a sensor.

In some embodiments the sensor is selected from the group consisting of: a strain gauge; a force sensing resistor; a piezo crystal; and combinations thereof.

In some embodiments the sensor is positioned between the glenoid fixation member and the scapula.

In some embodiments the sensor is positioned on the surface of the scapula.

In some embodiments the sensor is positioned on the glenoid cavity.

In some embodiments the sensor is positioned on the anterior and/or posterior surface of the scapula.

In some embodiments the sensor is positioned on an internal portion of the scapula.

In some embodiments the pressure sensing system comprises a communication subsystem, wherein the communication subsystem is configured to generate a pressure sensor signal corresponding to the pressure measured between the glenoid facing surface of the glenoid member and a glenoid cavity of a scapula.

In some embodiments the communication subsystem comprises a wireless communication element.

In some embodiments the wireless communication element comprises a wireless transceiver operating on a frequency band selected from the group consisting of: 30-300 kHz, 300-3000 kHz, 3-30 MHz, 30-300 MHz, 300-3000 MHz, 3-30 GHz and 30-300 GHz.

In some embodiments the at least one attachment member comprises a pressure sensor, wherein the pressure sensor is operationally coupled to the pressure sensing system.

In some embodiments a biasing mechanism, wherein the biasing mechanism biases the pressure sensor in an outward direction from the glenoid facing surface.

In some embodiments the outward direction is a medial direction.

In some embodiments the biasing mechanism is a spring.

In some embodiments the biasing mechanism is selected from the group consisting of: a rubber plug, a foam plug and a plastic plug.

In another aspect an implantable shoulder prosthesis, comprises: a glenoid member comprising: a glenoid joint surface; and at least one glenoid fixation member attached to the glenoid member, the at least one glenoid fixation member comprising an elongated arm extending from the glenoid member to a location on a scapular surface, said scapular surface comprising an anterior, posterior or both anterior and posterior surface of the scapula.

In some embodiments the implantable shoulder prosthesis is constructed and arranged to prevent the scapula from fracture.

In some embodiments the implantable shoulder prosthesis is implantable in a two legged mammal.

In some embodiments the implantable shoulder prosthesis is implantable in a human being.

In some embodiments the implantable shoulder prosthesis is constructed and arranged to be of a size for being implantable in a human being.

In some embodiments the glenoid member further comprises a medial surface opposite the glenoid joint surface.

In some embodiments the medial surface is constructed and arranged to contact a glenoid cavity of a mammalian scapula.

In some embodiments the glenoid member comprises at least one fin projecting from the medial surface.

In some embodiments the glenoid member comprises at least one peg projecting from the medial surface.

In some embodiments the glenoid member comprises at least one peg projecting from the medial surface.

In some embodiments the glenoid member comprises a material selected from the group of materials consisting of: cobalt-chrome; titanium; stainless steel; tantalum; polyethylene; silicon; nylon; and combinations thereof.

In some embodiments the glenoid member comprises a laminated construction.

In some embodiments said laminated construction comprises at least two materials selected from the group of materials consisting of: cobalt-chrome; titanium; stainless steel; tantalum; polyethylene; silicon; nylon; plastic; elastomer; silicone; and combinations thereof.

In some embodiments said laminated construction comprises at least a compressible material and an incompressible material.

In some embodiments the glenoid member comprises a first portion and a second portion, the first portion comprising the glenoid joint surface and the second portion comprising a surface opposite the glenoid joint surface.

In some embodiments the first portion is fixedly attached to the second portion.

In some embodiments the first portion of the glenoid member is a replaceable element.

In some embodiments the glenoid member comprises a first portion and a second portion connected together via a hinge.

In some embodiments the hinge extends in a superior-inferior direction.

In some embodiments the hinge extends in an anterior-posterior direction.

In some embodiments the hinge is constructed and arranged to allow a head of a humerus to dislocate prior to causing a fracture in the implantable shoulder prosthesis or the scapula.

In some embodiments the first portion and the second portion flex about a longitudinal axis of the hinge.

In some embodiments the hinge is positioned at a central portion of the glenoid member.

In some embodiments the hinge comprises a rubber material.

In some embodiments the hinge is constructed and arranged to prevent fracture of the scapula.

In some embodiments the glenoid member comprises a first portion, a second portion, a third portion and a fourth portion, wherein each of the first through fourth portions are connected together via a hinge.

In some embodiments the hinge comprises a first hinge portion that extends in a superior-inferior direction and a second hinge portion that extends in an anterior-posterior direction.

In some embodiments a torsional stiffness of the first hinge portion is greater than a torsional stiffness of the second hinge portion.

In some embodiments the glenoid joint surface of the glenoid member is constructed and arranged to provide a bearing surface for a head portion of a humerus.

In some embodiments the head portion of the humerus is an artificial implant.

In some embodiments the glenoid joint surface of the glenoid member is concave.

In some embodiments the glenoid joint surface of the glenoid member is convex.

In some embodiments the glenoid joint surface of the glenoid member comprises a concave cross section relative to a superior-inferior direction of extension.

In some embodiments the humeral head surface of the glenoid member comprises a concave cross section relative to an anterior-posterior direction of extension.

In some embodiments the humeral head surface of the glenoid member comprises a concave cross section relative to a superior-inferior direction of extension and an anterior-posterior direction of extension.

In some embodiments the at least one glenoid fixation member is constructed and arranged to prevent the scapula from fracture.

In some embodiments the at least one glenoid fixation member is constructed and arranged to hold fractured portions of the scapula together.

In some embodiments the at least one glenoid fixation member is less than about 10 cm in length.

In some embodiments the at least one glenoid fixation member is less than about 15 cm in length.

In some embodiments the at least one glenoid fixation member is less than about 20 cm in length.

In some embodiments the at least one glenoid fixation member comprises a material selected from the group of materials consisting of: cobalt-chrome; titanium; stainless steel; tantalum; polyethylene; silicon; nylon; and combinations thereof.

In some embodiments the glenoid member and the at least one glenoid fixation member comprise materials each having a different stiffness.

In some embodiments the implantable shoulder prosthesis is at least one attachment mechanism, the at least one attachment mechanism constructed and arranged to secure the at least one glenoid fixation member to the scapular surface.

In some embodiments the at least one attachment mechanism comprises a bone screw.

In some embodiments the at least one attachment mechanism comprises a molly bolt.

In some embodiments the at least one attachment mechanism comprises an attachment mechanism selected from the group consisting of: a screw; a machine screw; a nut; a lock nut; a rivet; a bolt; a washer; and combinations thereof.

In some embodiments the at least one attachment mechanism comprises a material selected from the group of materials consisting of: cobalt-chrome; titanium; stainless steel; tantalum; polyethylene; silicone; nylon; and combinations thereof.

In some embodiments the at least one glenoid fixation member is removably attached to the glenoid member.

In some embodiments the at least one glenoid fixation member is attached to a central region of the glenoid side surface of the glenoid member.

In some embodiments the at least one glenoid fixation member is attached to an off-central region of the glenoid surface of the glenoid member.

In some embodiments the at least one glenoid fixation member is attached to an outer side surface of the glenoid member.

In some embodiments a side surface of the at least one glenoid fixation member is aligned with an outer side surface of the glenoid member.

In some embodiments the at least one glenoid fixation member comprises a first fixation member and a second fixation member.

In some embodiments the first fixation member is secured to the anterior surface of the scapula and the second fixation member is secured to the posterior surface of the scapula.

In some embodiments the first and second fixation members each comprise at least one attachment orifice constructed and arranged to receive an attachment mechanism.

In some embodiments the at least one attachment orifice of each of the first and second fixation members is aligned with each other.

In some embodiments the implantable shoulder prosthesis is an attachment mechanism, wherein the attachment mechanism is constructed and arranged to engage the at least one attachment orifice of each of the first and second stabilizing members to secure the first and second stabilizing members to the opposing anterior and posterior surfaces of the scapula.

In some embodiments the at least one glenoid fixation member comprises at least a rigid portion.

In some embodiments the at least one glenoid fixation member comprises at least a semi-rigid portion.

In some embodiments the at least one glenoid fixation member comprises at least a flexible portion.

In some embodiments the at least one glenoid fixation member comprises at least a rigid portion and a non-rigid portion.

In some embodiments the elongated arm of the at least one glenoid fixation member is constructed and arranged to conform to the scapular surface.

In some embodiments the scapula is a human scapula.

In some embodiments the at least one glenoid fixation member is machined to approximate the contour of the scapula.

In some embodiments the at least one glenoid fixation member is machined based on a patient image.

In some embodiments the patient image is selected from the group consisting of: X-Ray; CtScan; MRI, Nuclear Image; Ultrasound Image; Electromagnetic Image; and combinations thereof.

In some embodiments the at least one glenoid fixation member comprises at least a rigid portion.

In some embodiments the at least one glenoid fixation member comprises at least a flexible portion.

In some embodiments the at least one glenoid fixation member comprises at least a malleable portion.

In some embodiments the at least a malleable portion is constructed and arranged to be plastically deformed prior to attaching the at least one glenoid fixation member to the scapula.

In some embodiments the at least one glenoid fixation member comprises a rubber coating.

In some embodiments the at least one glenoid fixation member comprises a laminated construction.

In some embodiments said laminated construction comprises at least two materials selected from the group of materials consisting of: cobalt-chrome; titanium; stainless steel; tantalum; polyethylene; silicon; nylon; plastic; elastomer; silicone; and combinations thereof.

In some embodiments said laminated construction comprises at least a compressible material and an incompressible material.

In some embodiments the implantable shoulder prosthesis has at least one attachment element protruding from the at least one glenoid fixation member.

In some embodiments the attachment element is integral with the at least one glenoid fixation member.

In some embodiments the at least one glenoid fixation member comprises at least one attachment orifice constructed and arranged to receive an attachment mechanism.

In some embodiments the implantable shoulder prosthesis has at least one attachment mechanism, wherein the at least one attachment mechanism is constructed and arranged to engage the at least one attachment orifice to secure the at least one glenoid fixation member to the scapular surface.

In some embodiments the at least one attachment orifice comprises a first attachment orifice and a second attachment orifice.

In some embodiments the first attachment orifice and the second attachment orifice are spaced apart from each other.

In some embodiments the at least one attachment orifice comprises a screw hole.

In some embodiments the at least one attachment orifice comprises a first attachment orifice and a second attachment orifice, and wherein the elongated arm comprises first and second arm portions that each extend from the elongated arm.

In some embodiments the first attachment orifice is positioned along the first arm portion and the second attachment orifice is positioned along the second arm portion.

In some embodiments a planar surface of the first arm portion is offset from a planar surface of the second arm portion.

In some embodiments the implantable shoulder prosthesis is an adhesive material.

In some embodiments the adhesive material secures the at least one fixation member to the scapular surface.

In some embodiments the implantable shoulder prosthesis is at least one attachment mechanism, the at least one attachment mechanism constructed and arranged to further secure the at least one glenoid fixation member to the scapular surface.

In some embodiments the adhesive material secures the glenoid member to a glenoid cavity of the scapula.

In some embodiments the adhesive resides between the second surface and the glenoid cavity.

In some embodiments the glenoid member comprises at least one projection extending from the second surface, and wherein the adhesive surrounds the projection.

In some embodiments the adhesive material is a glue material.

In some embodiments the adhesive material is a cement material.

In some embodiments the implantable shoulder prosthesis is at least one cushion member connected to the at least one glenoid fixation member.

In some embodiments the at least one cushion member comprises a material selected from the group consisting of: a foam material; a rubber material; a plastic material; and combinations thereof.

In some embodiments the glenoid member has an anterior end and a posterior end, said prosthesis further comprising a bioabsorbable constraint member extending from said glenoid member anterior end or said glenoid member posterior end, wherein the bioabsorbable constraint member bioabsorbs when present in a human body.

In some embodiments the bioabsorbable constraint member limits rotation of a humerus bone.

In some embodiments the bioabsorbable constraint member increases rotational movement of the humerus bone in proportion to the bioabsorption of the bioabsorbable constraint member.

In some embodiments the bioabsorbable constraint member increases rotational movement of the humerus bone when the bioabsorbable constraint member is bioabsorbed.

In some embodiments the bioabsorbable constraint member bioabsorbed over a period of at least one week.

In some embodiments the bioabsorbable constraint member bioabsorbs over a period of at least one month.

In some embodiments the bioabsorbable constraint member bioabsorbs over a period of at least six months.

In some embodiments the bioabsorbable constraint member comprises a first bioabsorbable portion and a second bioabsorbable portion.

In some embodiments the first bioabsorbable portion and the second bioabsorbable portion have different rates of bioabsorption.

In some embodiments the implantable shoulder prosthesis is a coating.

In some embodiments the coating is constructed and arranged to promote tissue ingrowth and/or prevent wear.

In some embodiments the implantable shoulder prosthesis is glenoid bulking material.

In some embodiments the bulking material is selected from the group consisting of: bone; foam; plastic; cement; metal; and combinations thereof.

In some embodiments the implantable shoulder prosthesis is a support member attached on and/or near the glenoid cavity.

In some embodiments the implantable shoulder prosthesis is an attachment tool.

In some embodiments the attachment tool comprises a right angle screwdriver.

In some embodiments the attachment tool is powered.

In some embodiments the attachment tool comprises a wrench.

In some embodiments the handle is a curvilinear handle.

In some embodiments the handle is malleable.

In some embodiments the implantable shoulder prosthesis is a humeral implant.

In some embodiments the humeral implant comprises a convex mating surface.

In some embodiments the humeral implant comprises a concave surface.

In some embodiments the implantable shoulder prosthesis is a securing assembly constructed and arranged to attach tissue to at least one glenoid fixation member.

In some embodiments the tissue comprises rotator cuff tissue.

In some embodiments the securing assembly is constructed and arranged to allow suture to pass therethrough.

In some embodiments the securing assembly comprises a loop.

In some embodiments the securing assembly comprises mesh.

In some embodiments the mesh is Dacron mesh.

In another aspect a method of manufacturing an implantable shoulder prosthesis comprises: providing a glenoid member having a lateral facing surface and a medial facing surface; imaging a topography of a scapula; and forming at least one stabilizing member based on the topography of a scapula, wherein the at least one stabilizing member is attached to the glenoid member.

In some embodiments the at least one stabilizing member comprises an elongated arm extending from the glenoid member in a direction transverse to the medial facing surface.

In some embodiments the imaging of the topography of a scapula is performed by a magnetic resonance imaging system.

In some embodiments the imaging of the topography of a scapula is performed by a computed tomography imaging system.

In some embodiments the imaging of the topography of a scapula is performed by an imaging system selected from the group consisting of: computed tomography; X-ray; NMR; MRI; ultrasound imaging device; infrared imaging device; and combinations thereof.

BRIEF DESCRIPTION OF THE DRAWINGS

The foregoing and other objects, features and advantages of the invention will be apparent from the more particular description of preferred embodiments, as illustrated in the accompanying drawings in which like reference characters refer to the same parts throughout the different views. The drawings are not necessarily to scale, emphasis instead being placed upon illustrating the principles of the preferred embodiments.

FIG. 1A is an anterior facing environmental view of a left shoulder joint;

FIG. 1B is a posterior facing environmental view of a left shoulder joint;

FIG. 2 is an anterior facing environmental view of an implantable shoulder prosthesis comprising a dampener in accordance with embodiments of the present invention;

FIGS. 10a and 10b are top perspective views of an implantable shoulder prosthesis in accordance with embodiments of the present invention;

FIG. 11 is top perspective view of an implantable shoulder prosthesis comprising a hinge in accordance with embodiments of the present invention;

FIGS. 12a, 12b and 12c illustrate a plurality of hinge configurations of the glenoid joint surface of the implantable shoulder prosthesis of FIG. 11 in accordance with embodiments of the present invention;

FIGS. 13a and 13b are top perspective views of an implantable shoulder prosthesis in accordance with embodiments of the present invention;

DETAILED DESCRIPTION OF VARIOUS EMBODIMENTS

Figure 1C:
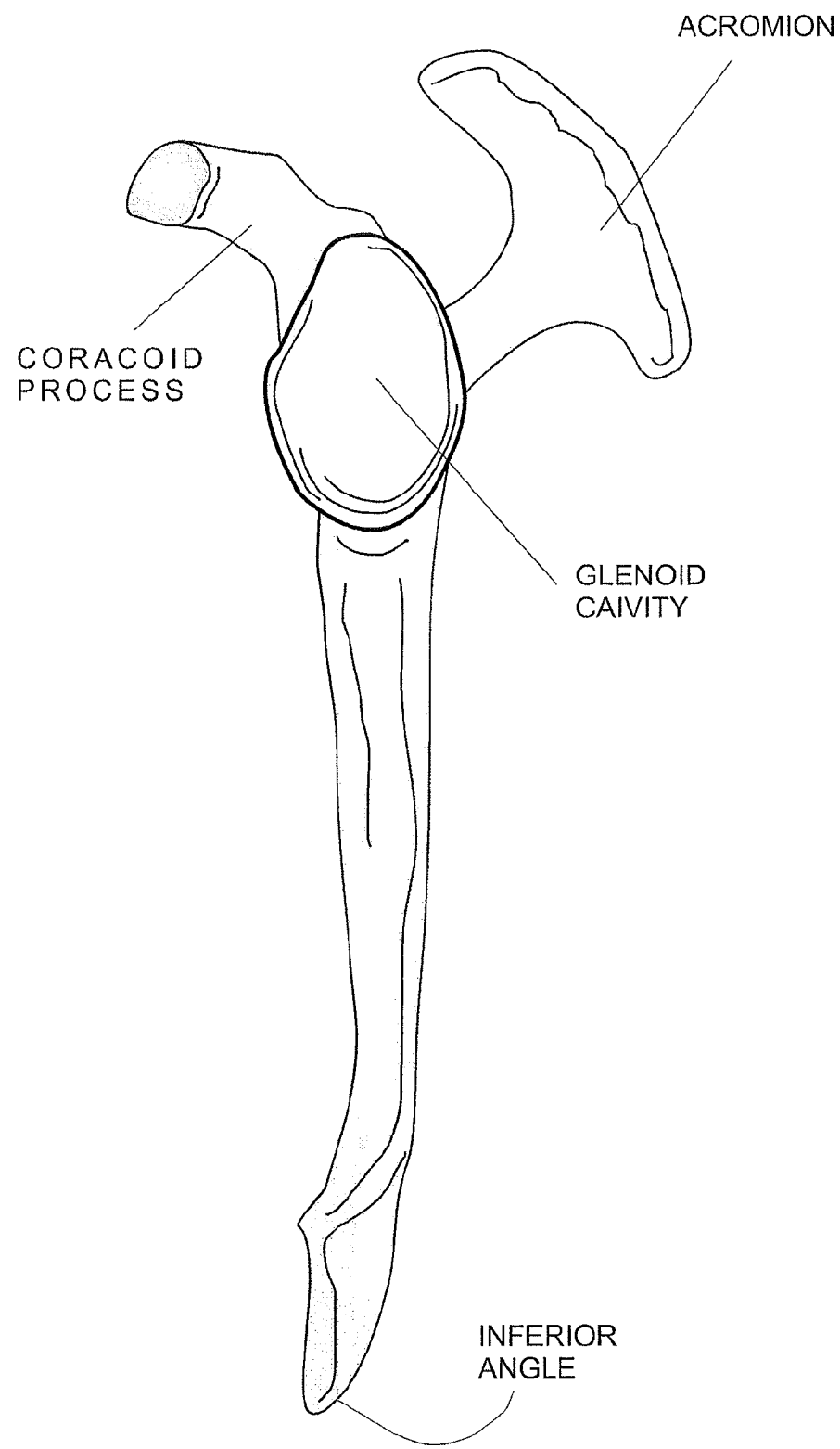
FIG. 1C is a lateral/medial facing view of a scapula.

Embodiments of the invention are described more fully hereinafter with reference to the accompanying drawings, in which exemplary embodiments of the invention are shown. The present invention may, however, be embodied in many different forms and should not be construed as limited to the example embodiments set forth herein. Rather, these exemplary embodiments are provided so that this disclosure will be thorough and complete. In the drawings, the sizes and relative sizes of objects may be exaggerated for clarity.

It will be understood that when an element or object is referred to as being "on," "connected to" or "coupled to" another element or object, it can be directly on, connected or coupled to the other element or object, or intervening elements or objects may be present. In contrast, when an element is referred to as being "directly on," "directly connected to" or "directly coupled to" another element or object, there are no intervening elements or objects present. As used herein, the term "and/or" includes any and all combinations of one or more of the associated listed items.

It will be understood that, although the terms first, second, etc. are used herein to describe various elements, these elements should not be limited by these terms. These terms are used to distinguish one element from another. For example, a first element could be termed a second element, and, similarly, a second element could be termed a first element, without departing from the scope of the present invention. As used herein, the term "and/or" includes any and all combinations of one or more of the associated listed items.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specifically the presence of stated features, integers, steps, operations, elements, and/or components, but do not preclude the presence or addition of one or more other features, integers, steps, operations, elements, components, and/or groups thereof.

FIG. 1a is an anterior facing environmental view of a shoulder joint, FIG. 1b is a posterior facing environmental view of a shoulder joint, and FIG. 1c is a lateral/medial facing view of a scapula. In human anatomy, a shoulder joint comprises the part of the body where a humeral bone (i.e., humerus) attaches to a shoulder blade (i.e., scapula). The humerus comprises a humeral head portion that interfaces with a glenoid cavity of a scapula, such that the humerus articulates with respect to the glenoid cavity of the scapula. The scapula forms the posterior located part of the shoulder girdle.

For purposes of the present disclosure, the terms "sagittal plane" and the like, when referring to portions of the human body, refers to an imaginary plane that travels vertically from the top to the bottom of the body, dividing the body into left and right portions.

For purposes of the present disclosure, the terms "coronal plane", "frontal plane" and the like, when referring to portions of the human body, refers to an imaginary plane that travels vertically from the top to the bottom of the body, dividing the body into anterior and posterior (e.g., belly and back) portions.

For purposes of the present disclosure, the terms "medial", "medial direction" and the like, when referring to anatomical terms of direction, refers to a direction that is transverse to the sagittal plane of a human body, and that extends in a direction toward the sagittal plane of a human body.

For purposes of the present disclosure, the terms "lateral", "lateral direction" and the like, when referring to anatomical terms of direction, refers to a direction that is transverse to the sagittal plane of a human body, and that extends in a direction away from the sagittal plane of a human body.

For purposes of the present disclosure, the terms "superior/inferior", "superior/inferior direction" and the like, when referring to anatomical terms of direction, refers to a direction that extends in upward and downward directions, through a superior angle of a scapula and an inferior angle of a scapula.

For purposes of the present disclosure, the terms "superior", "superior direction" and the like, when referring to anatomical terms of direction, refers to a direction that extends upward, through a superior angle of a scapula.

For purposes of the present disclosure, the terms "inferior", "inferior direction" and the like, when referring to anatomical terms of direction, refers to a direction that extends downward, through an inferior angle of a scapula.

FIG. 2 is an anterior facing environmental view of an implantable shoulder prosthesis comprising a dampener in accordance with embodiments of the present invention. A shoulder prosthesis 100 can comprise a glenoid member 101 having a glenoid joint member 103 and at least one glenoid fixation member 106.

The glenoid fixation member 106 can be constructed and arranged to attach the glenoid member 101 to a glenoid cavity of a scapula 110. For example, the glenoid fixation member 106 can extend from a medial face 122 of the glenoid member 101 in a medial direction MD, and may comprise a fin, a pin, a peg or a screw. Further, the glenoid fixation member 106 can be integral with the glenoid member 101, or may be a separate piece connected thereto. The glenoid fixation member 106 or portions thereof can be surrounded by a dampening material 108, which can absorb and dissipate an applied load force, thus reducing notching and chipping of bone and component loosening associated with the implantable shoulder prosthesis 100. In some embodiments, glenoid fixation member 106 is 10 cm, 15 cm, or 20 cm in length.

In one embodiment, a fin, such as a glenoid fin known to those of skill in the art, can be used to attach the glenoid member 101 to a scapula 110. In another embodiment, a pin, such as a glenoid pin known to those of skill in the art, can be used to attach the glenoid member 101 to a scapula 110. In another embodiment, a peg, such as a glenoid peg known to those of skill in the art, can be used to attach the glenoid member 101 to a scapula 110. In another embodiment, a screw, such as a glenoid screw known to those of skill in the art, can be used to attach the glenoid member 101 to a scapula 110.

The glenoid member 101 can further comprise a dampener 104, which is constructed and arranged to absorb a load force 116 transferred to the glenoid fixation members 106. In one embodiment, the dampener 104 absorbs a load force 116 applied to a glenoid joint surface 102 of the glenoid joint member 103, such that, a reduced load force is transferred to the glenoid fixation members 106. As a result of the dampening of the load force 116, notching and chipping of bone and component loosening associated with the implantable shoulder prosthesis 100 is reduced.

The dampener 104 may comprise a compressible material, for example, a rubber compound, plastic compound, a foam material, a silicon material and the like. The dampener 104 can further comprise a bone bonding material, which can be used to secure the glenoid joint member 103 to a glenoid cavity of a scapula 110. In one embodiment, the bone bonding material can comprise an elastomeric material. In another embodiment, the bone bonding material can comprise a flexible cement, such as the flexible bone composite disclosed in U.S. Ser. No. 11/148,193, filed on Jun. 9, 2005, by Kerr, et al., the content of which is incorporated herein by reference. In addition, the bone bonding material can be used to attach various components of a shoulder prosthesis to a humeral bone or a scapula 110.

The glenoid joint surface 102 of the glenoid joint member 103 can be constructed and arranged provide a bearing surface for a head portion 120 of a humeral member 118. The head portion 120 can comprise an artificial humeral head prosthetic or a humeral head of a human humeral bone.

In one embodiment, the glenoid joint surface 102 of the glenoid joint member 103 is concave, such that, the glenoid joint surface 102 is constructed and arranged to interface with a convex humeral joint surface of a head portion 120 of a humeral member 118. In another embodiment, the glenoid joint surface 102 of the glenoid joint member is convex, such that, the glenoid joint surface 102 is constructed and arranged to interface with a concave humeral joint surface of a head portion 120 of a humeral member 118 (e.g., reverse shoulder prosthetic). In these embodiments, the humeral member 118 can comprise a humeral bone of a human being or an artificial humeral prosthetic, or combination thereof.

In some embodiments, prosthesis 100 can include a coating, not shown but typically on one or more portions of prosthesis 100 outer surface. The coating can be selected from the group consisting of: a lubricous, an anti-rejection agent, an anti-inflammatory agent, an anti-bacterial coating; and combinations of these. Additionally, one or more coatings can be included to promote bone ingrowth and/or prevent wear.

Figure 3A:
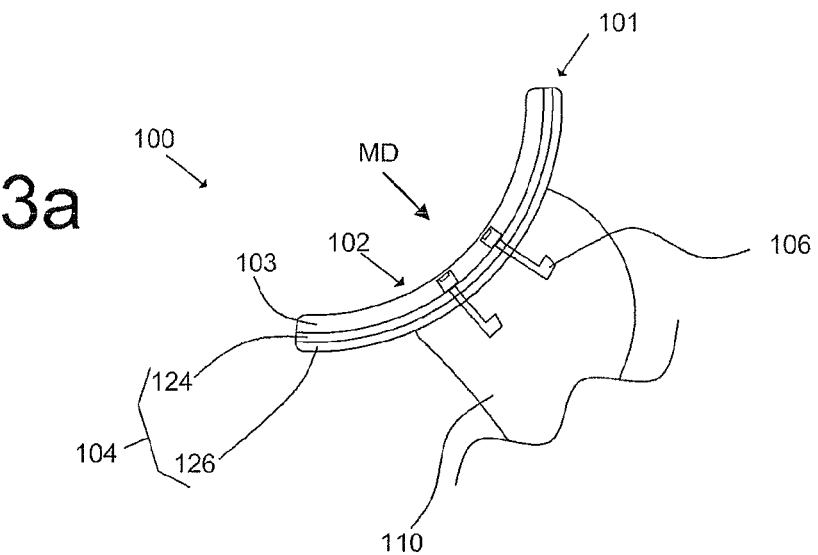
FIG. 3A is a side view of an implantable shoulder prosthesis comprising a dampener in accordance with embodiments of the present invention.
Figure 3B:
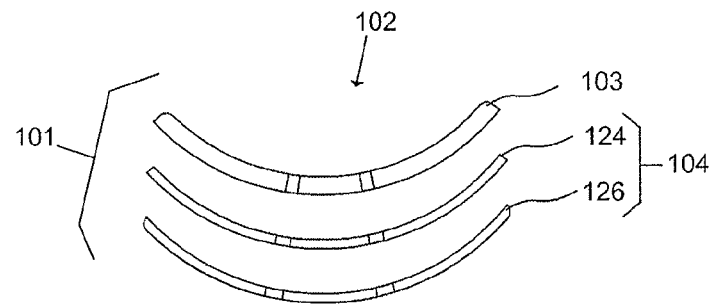
FIG. 3B is an exploded side view of the implantable shoulder prosthesis of FIG. 3A in accordance with embodiments of the present invention.

FIG. 3a is a side view of an implantable shoulder prosthesis comprising a dampener in accordance with embodiments of the present invention, and FIG. 3b is an exploded side view of the implantable shoulder prosthesis of FIG. 3a in accordance with embodiments of the present invention. In one embodiment, a glenoid member 101 of a shoulder prosthesis 100 comprises a glenoid joint member 103 and a dampener 104 having a first dampening portion 124 and a second dampening portion 126.

In one embodiment, the first dampening portion 124 comprises a compression ratio greater than a compression ratio of the second dampening portion 126. In another embodiment, the first dampening portion 124 comprises a compression ratio less than a compression ratio of the second dampening portion 126. In another embodiment, the first dampening portion 124 comprises a compression ratio equal to a compression ratio of the second dampening portion 126.

The first dampening portion 124 and the second dampening portion 126 may comprise a compressible material, for example, a rubber compound, plastic compound, a foam material, a silicon material and the like. In one embodiment, the first dampening portion 124 comprises a compressible material different from a material of the second dampening portion 126.

The shoulder prosthesis 100 may further comprise a glenoid fixation member 106 that is constructed and arranged to attach the glenoid member 101 to a scapula 110. In this embodiment, the glenoid fixation member 106 comprises a rotatable anchor; however, other types glenoid fixation members 106 may be used to attach the glenoid member 101 to a scapula 110.

Figure 3C:
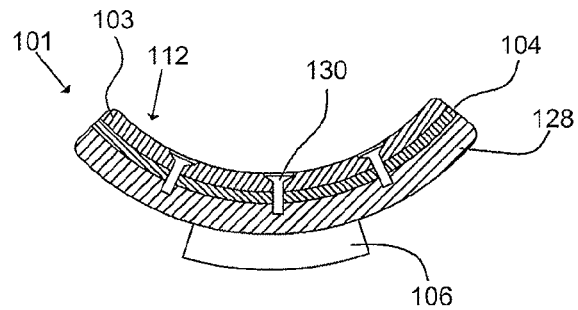
FIG. 3C is a side view of an implantable shoulder prosthesis comprising a replaceable glenoid joint surface in accordance with embodiments of the present invention.

FIG. 3c is a side view of an implantable shoulder prosthesis comprising a replaceable glenoid joint surface in accordance with embodiments of the present invention. In this embodiment, a glenoid member 101 of a shoulder prosthesis 100 comprises a glenoid joint member 103 that is removably attached to a rigid glenoid component 128. The glenoid joint member 103 can be attached to the rigid glenoid component 128 by a screw 130. Other means for attaching the glenoid joint member 103 to the rigid glenoid component can be used, for example, hooks, clips, adhesives, engaging surfaces, and the like. The glenoid member 101 may further comprise a dampener 104 positioned between the glenoid joint member 103 and the rigid glenoid component 128. In this embodiment, the glenoid fixation member 106 comprises a fin; however, other types glenoid fixation members 106 may be used to attach the glenoid member 101 to a scapula 110.

Figure 4:
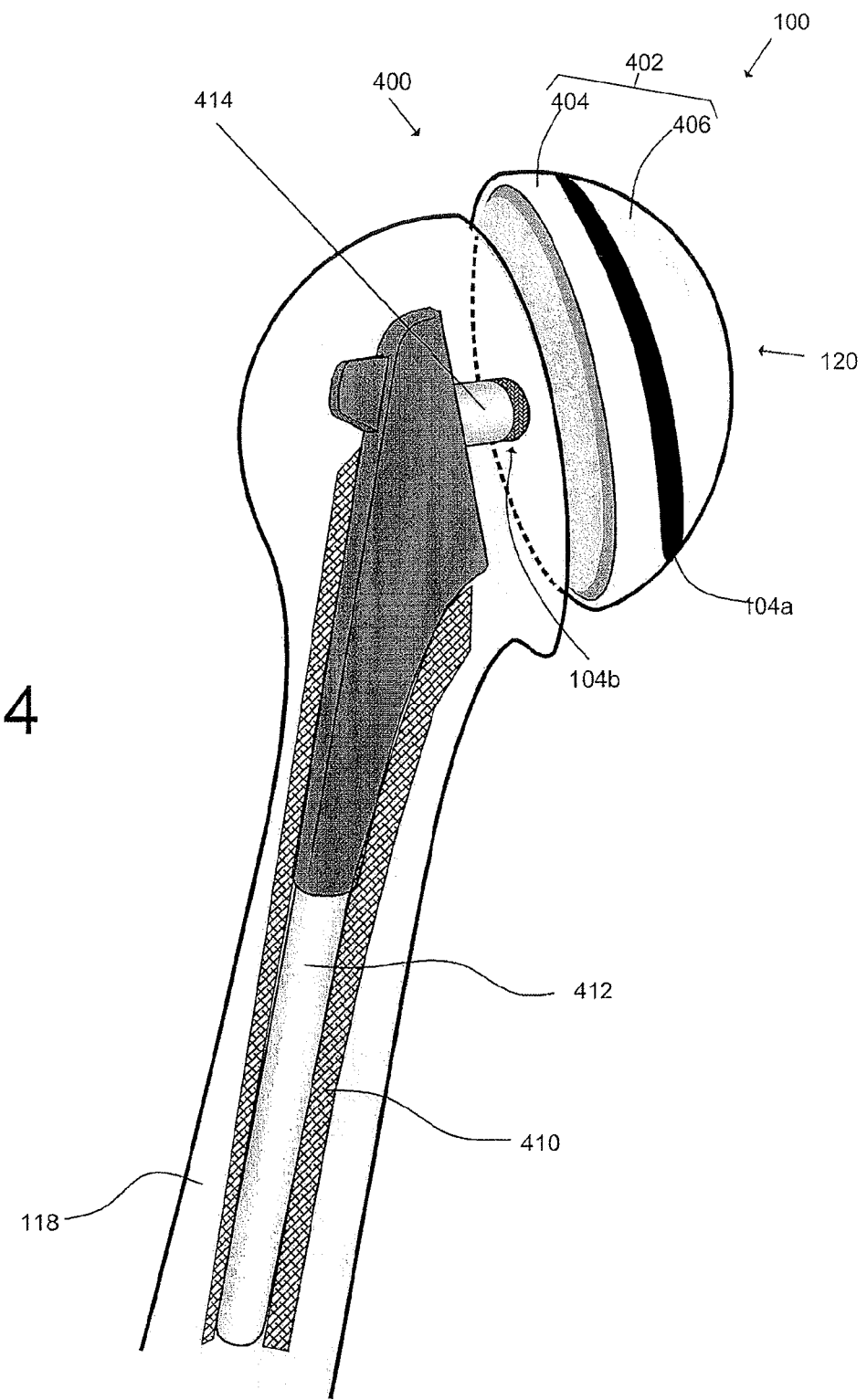
FIG. 4 is a side view of an implantable shoulder prosthesis comprising a humeral prosthetic having a dampener in accordance with embodiments of the present invention.

FIG. 4 is a side view of an implantable shoulder prosthesis comprising a humeral prosthetic having a dampener in accordance with embodiments of the present invention. A shoulder prosthesis 100 can comprise an implantable humeral head 402 adapted to interface with a glenoid joint of a scapula. The glenoid joint can comprise an implantable glenoid component or a glenoid cavity of a human scapula.

In one embodiment, the humeral head 402 comprises a first head portion 404 and a second head portion 406. The humeral head 402 can further comprise a dampener 104a connected between the first head portion 404 and the second head portion 406 of the humeral head 402. The humeral head 402 can be further connected to a humeral stem 412 at a connection rod 414. In one embodiment, the connection rod 414 comprises a dampener 104b.

The humeral stem 412 can be implanted in a humerus 118, and secured therein with an adhesive material 410. In one embodiment, the adhesive material 410 comprises a flexible dampening material, an adhesive cement, an adhesive glue and the like.

In these embodiments, the dampeners 104a and 104b and the dampening material 410 can reduce a load force transferred to a glenoid joint of a scapula, thus reducing notching and chipping of bone and component loosening associated with the implantable shoulder prosthesis 100.

Figure 5:
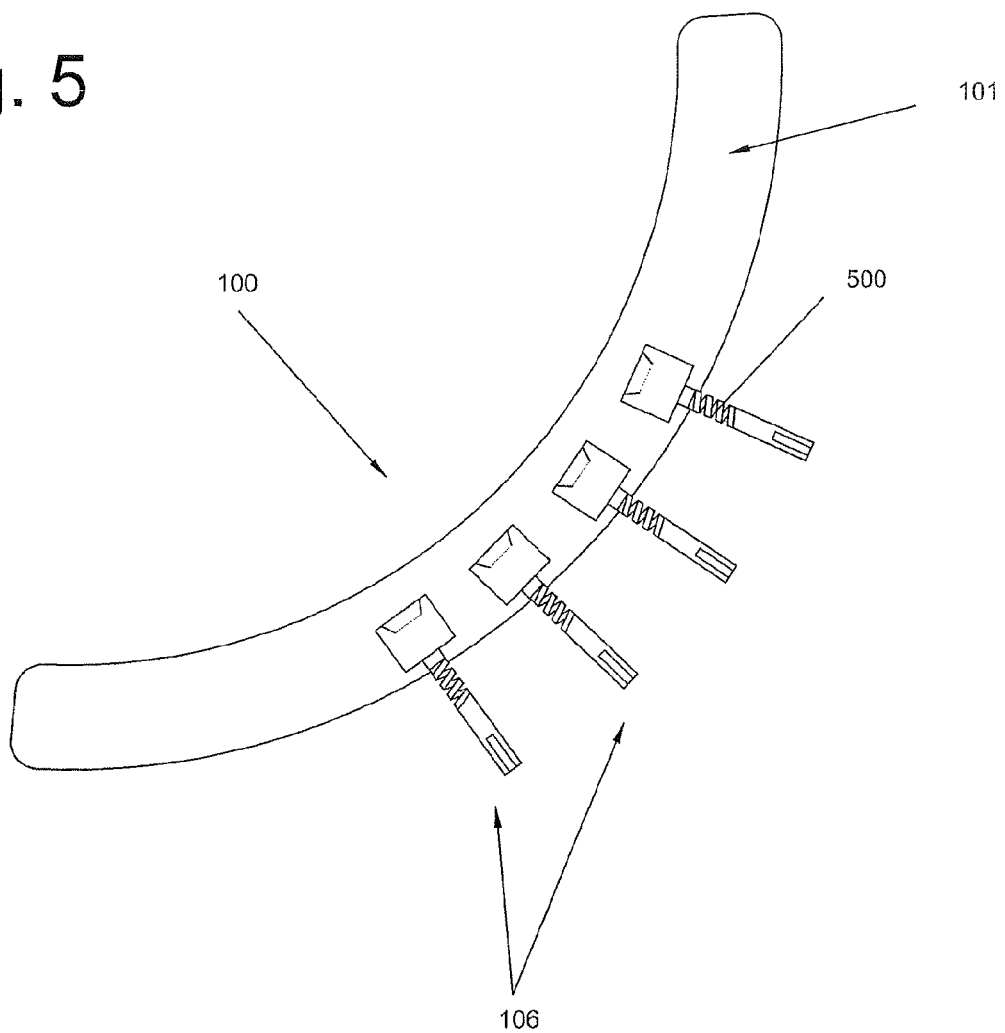
FIG. 5 is a side view of an implantable shoulder prosthesis comprising a plurality of fixation members in accordance with embodiments of the present invention.

FIG. 5 is a side view of an implantable shoulder prosthesis comprising a plurality of fixation members in accordance with embodiments of the present invention. An implantable shoulder prosthesis 100 can further comprise a glenoid member 101 and a plurality of glenoid fixation members 106. The glenoid fixation members can extend into a scapula 110 in a medial direction MD.

In this embodiment, the glenoid fixation member 106 comprises a spring 500, which is capable of absorbing and dissipating an applied load force 116. In one embodiment, the spring 500 is integral with the glenoid fixation member 106; however, in other embodiments, the spring 500 can be separate from the glenoid fixation member 106. As a result, the glenoid fixation member 106 can comprise a rigid portion and a flexible portion.

Figures 6A, 6B:
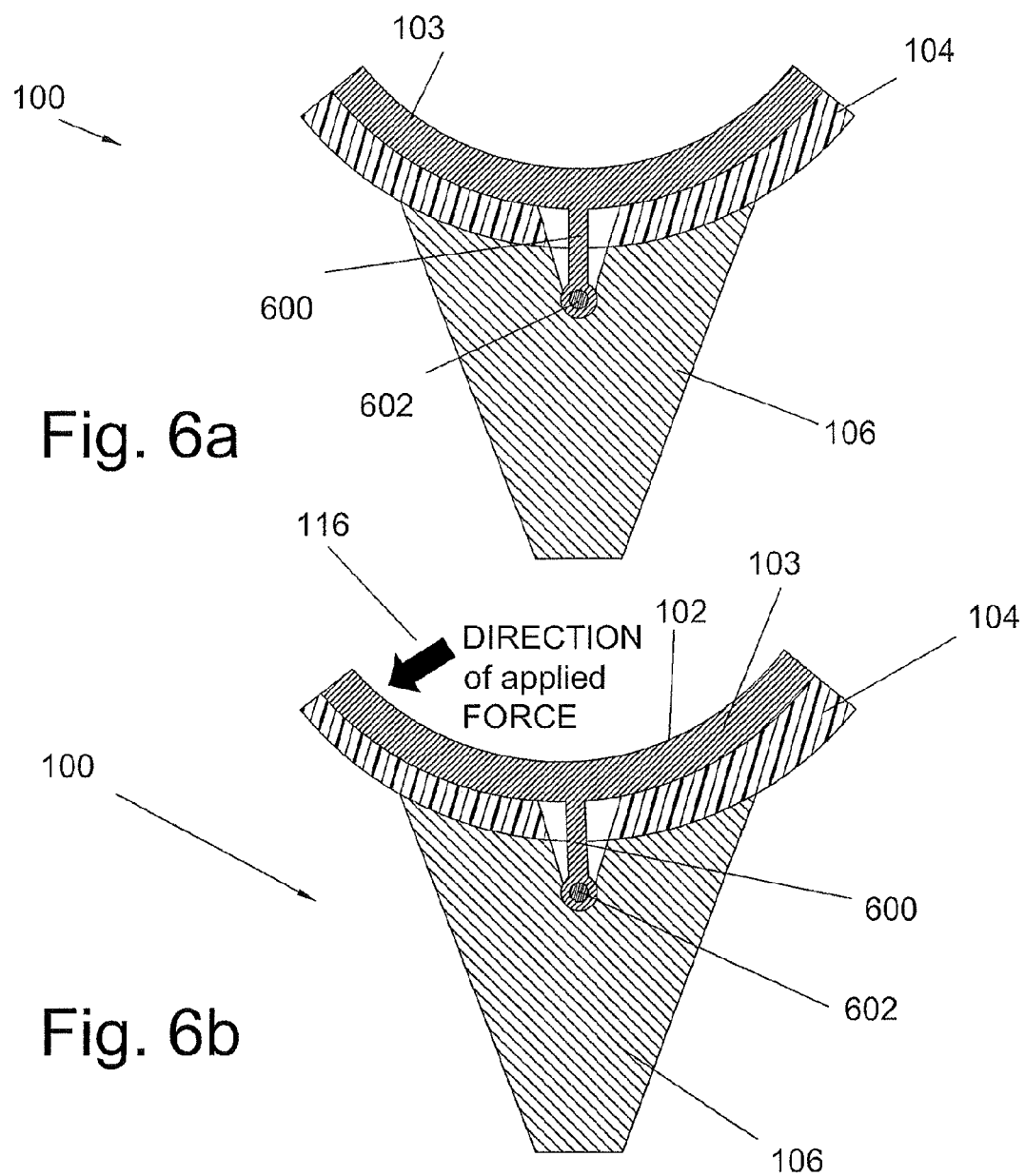
FIG. 6a is a side view of an implantable shoulder prosthesis comprising an articulating glenoid joint member in accordance with embodiments of the present invention.
FIG. 6b is a side view of the implantable shoulder prosthesis of FIG. 6a illustrating an applied load force.

FIG. 6a is a side view of an implantable shoulder prosthesis comprising an articulating glenoid joint member in accordance with embodiments of the present invention, and FIG. 6b is a side view of the implantable shoulder prosthesis of FIG. 6a illustrating an applied load force. An implantable shoulder prosthesis 100 can comprise a glenoid joint member 103, a dampener 104 and a glenoid fixation member 106. In this embodiment, the glenoid fixation member 106 is a fin; however, other types glenoid fixation members 106 may be used to attach the glenoid member 101 to a scapula 110.

The glenoid joint member 103 can comprise a hinge arm 600 that is connected to the glenoid fixation member 106 at hinged pin joint 602. In this embodiment, the dampener 104 is positioned between the glenoid joint member 103 and the glenoid fixation member 106 so as to absorb and dissipate an applied load force 116. For example, referring to FIG. 6b, when a load force is applied off-center to a glenoid joint surface 102 of the glenoid joint member 103, a portion of the dampener 104 absorbs the applied load force 116, allowing the glenoid joint member 103 to articulate with respect to the hinged pin joint 602. As a result, a reduced load force is transferred from the glenoid joint member 103 to the glenoid fixation member 106.

Figure 7:
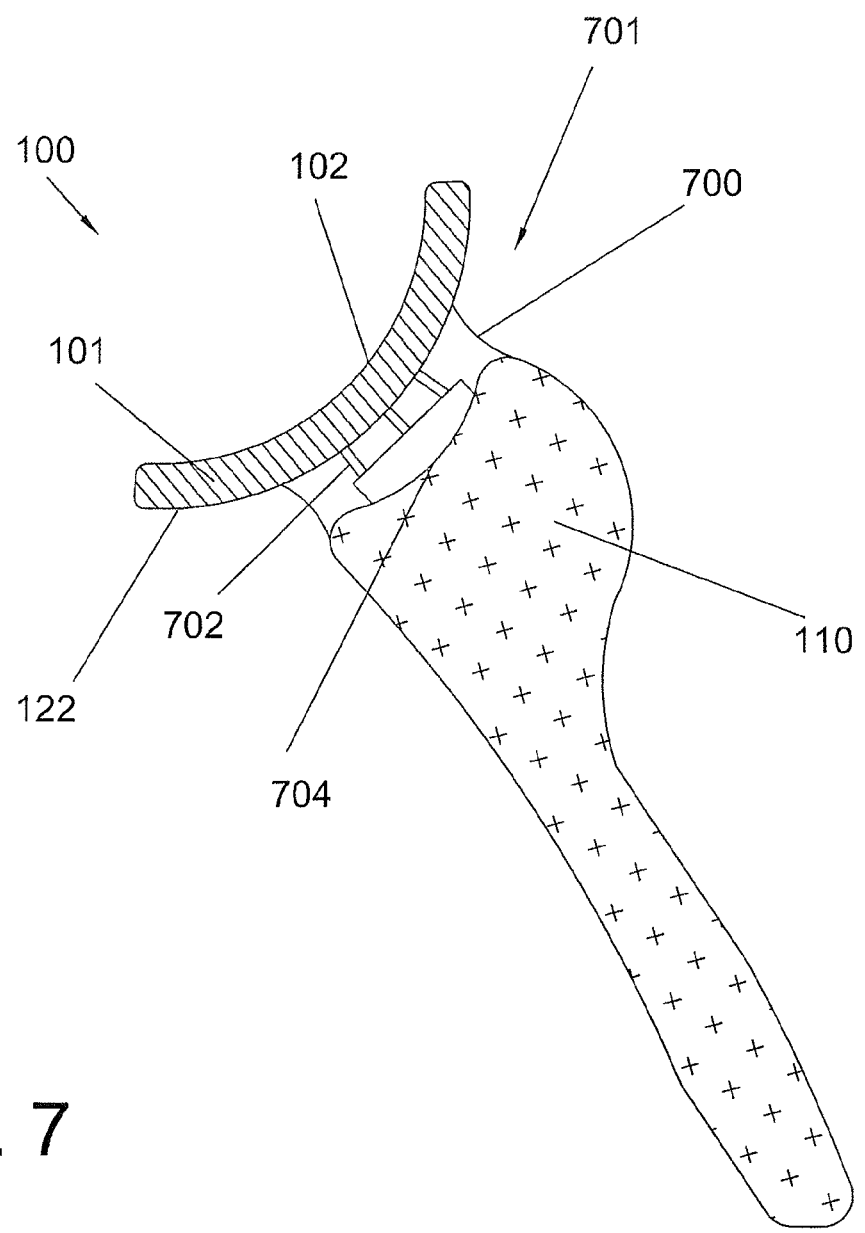
FIG. 7 is a top perspective view of an implantable shoulder prosthesis comprising a dampening system in accordance with embodiments of the present invention.

FIG. 7 is a top perspective view (a view in an inferior direction from a location superior to the patient's shoulder joint) of an implantable shoulder prosthesis comprising a dampening system in accordance with embodiments of the present invention. An implantable shoulder prosthesis 100 can comprise a glenoid member 101 and a dampening system 701.

The dampening system 701 may comprise at least one piston 702 connected to a hydraulic or pneumatic assembly 704, which is positioned between a medial face 122 of the glenoid member 101 and a scapula 110. The dampening system 701 is constructed and arranged to absorb and dissipate a load force 116, such as to the load force shown in FIG. 6b, applied to a glenoid joint surface 102 of the glenoid member 101.

In this embodiment, the dampening system 701 is surrounded by a protective membrane 700. The protective membrane 700 can comprise a compressible material, for example, a rubber compound, plastic compound, a foam material, a silicon material and the like. In some embodiments, the protective membrane 700 is further constructed and arranged to absorb and dissipate a load force 116 that is applied to the glenoid joint surface 102 of the glenoid member 101. In an alternative embodiment, a fluid filled reservoir can be used as a shock absorbing assembly. In another alternative embodiment, a spring can be used as a shock absorbing assembly, such as a spring selected from the group consisting of: torsional, compression, constant force, and/or Belleville springs.

Figure 8:
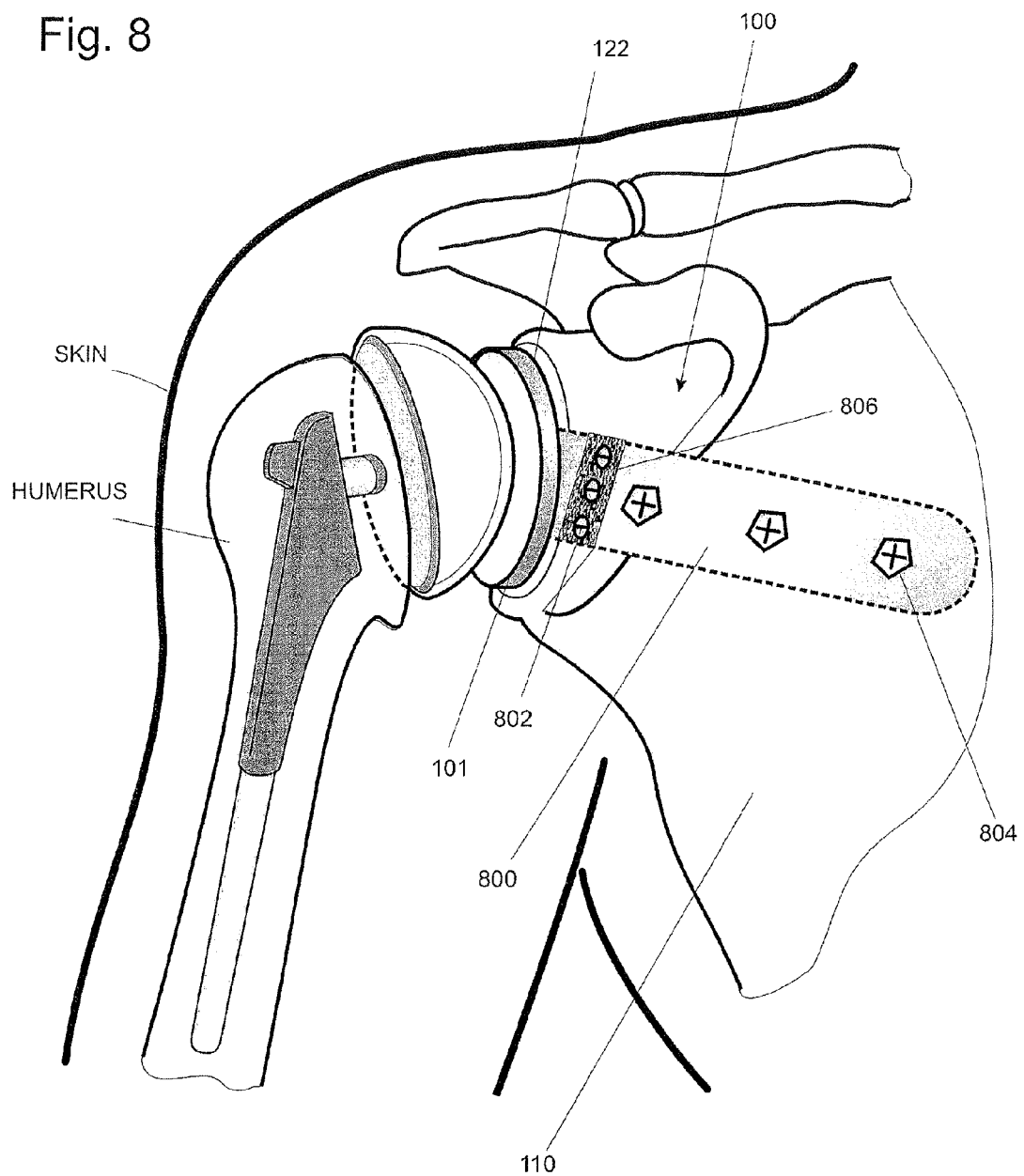
FIG. 8 is an anterior facing environmental view of an implantable shoulder prosthesis comprising a dampener and an extending glenoid fixation member, in accordance with embodiments of the present invention.

FIG. 8 is an anterior facing environmental view of an implantable shoulder prosthesis comprising a dampener in accordance with embodiments of the present invention. A shoulder prosthesis 100 can further comprise a glenoid member 101 having at least one stabilizing member 800 extending from the glenoid member 101 in a medial direction MD. In another embodiment, the stabilizing member 800 extends from the glenoid member 101 in a direction that is transverse to the medial face 122 of the glenoid member 101.

The stabilizing member 800 can comprise at least one attachment orifice constructed and arranged to receive an attachment mechanism 804, such as, a screw, bolt and washer, or molly bolt. For example, the attachment mechanism 804 can pass through the attachment orifice and into a scapula 110. When engaged, the attachment mechanism 804 operates to secure the stabilizing member 800 to a lateral surface of a scapula 110. In one embodiment, the lateral surface is an anterior surface of a scapula 110. Alternatively or additionally, the lateral surface is a posterior surface of a scapula 110.

In another embodiment, the stabilizing member 800 can further comprise a Dacron or other biocompatible mesh material 806 for attaching rotator cuff muscles and tendons thereto. In another embodiment, the stabilizing member 800 can further comprise a suture clasp 802 or a plurality thereof for attaching rotator cuff muscles and tendons thereto.

Figure 9A:
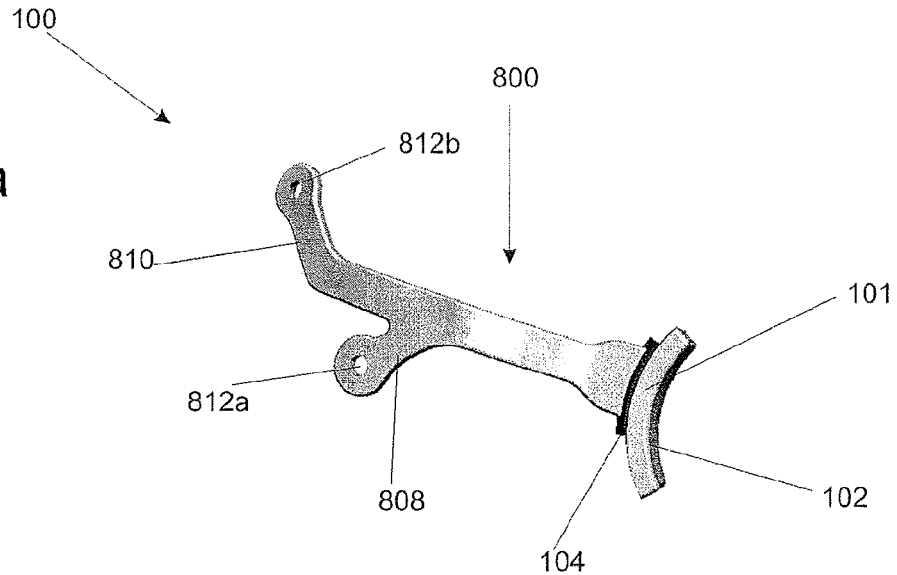
FIGS. 9a and 9b are 3-dimensional views of an implantable shoulder prosthesis in accordance with embodiments of the present invention.
Figure 9B:
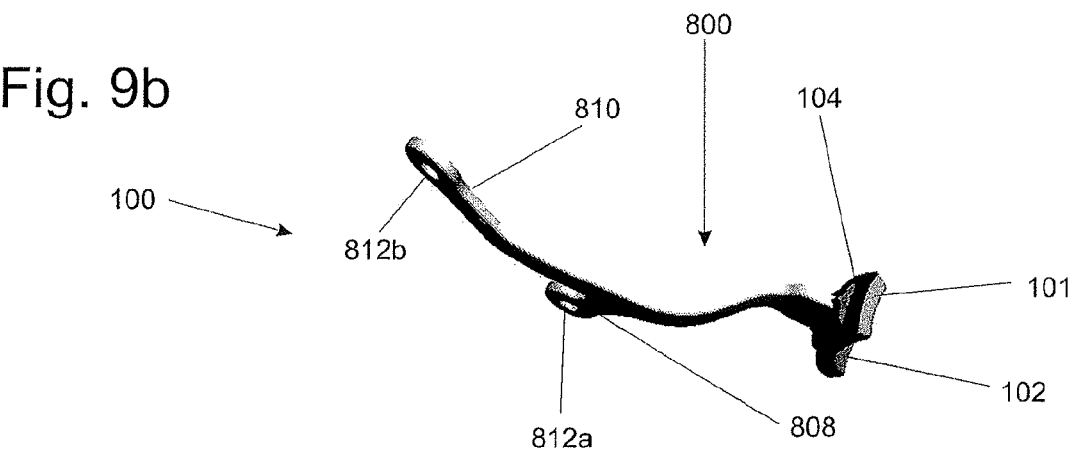

FIGS. 9a and 9b are 3-dimensional views of an implantable shoulder prosthesis in accordance with embodiments of the present invention. A shoulder prosthesis 100 can further comprise a glenoid member 101 and at least one stabilizing member 800 attached thereto. In this embodiment, the stabilizing member 800 is attached to a central region of the medial face of the glenoid member 101. A dampener, 104, may be positioned between glenoid member 101 and stabilizing member 800 such as to absorb shock and/or allow flexing of glenoid member 101 relative to stabilizing member 800.

The stabilizing member 800 can comprise an elongated arm having at least one attachment orifice, such as at least one of attachment orifice 812a or 812b positioned thereon, which is constructed and arranged to receive an attachment mechanism, such as a screw, bolt, rivet or other element for passing through attachment orifice 812a or 812b and into scapula 110. When engaged, the attachment mechanism operates to secure the stabilizing member 800 to a lateral surface of a scapula 110. In one embodiment, the elongated arm of the stabilizing member 800 comprises both first and second attachment orifices 812a and 812b, which are spaced apart from each other as shown.

In one embodiment, attachment orifices 812a or 812b comprises a non-threaded screw hole. In another embodiment, attachment orifices 812a or 812b comprises a threaded screw hole.

The elongated arm of the stabilizing member 800 can further comprise a first arm portion 808 and a second arm portion 810. In one embodiment, a first attachment orifice 812a is positioned along the first arm portion 808 and a second attachment orifice 812b is positioned along the second arm portion 810. In this embodiment, a planar surface of the first arm portion 808 can be offset from a planar surface of the second arm portion 810.

The implantable shoulder prosthesis 100 can further comprise an adhesive material that secures the stabilizing member 800 to a lateral surface of a scapula 110. The implantable shoulder prosthesis 100 can further comprise an adhesive material that secures the glenoid member 101 to a glenoid cavity of a scapula 110. The adhesive material can comprise a glue material, a cement material, a bone bonding material or a combination thereof.

In one embodiment, the glenoid joint surface 102 of the glenoid member 101 is concave, such that, the glenoid joint surface 102 is constructed and arranged to interface with a convex humeral head portion of a humeral member. In another embodiment, the glenoid joint surface 102 of the glenoid member 101 comprises a concave cross section relative to a superior-inferior direction of extension. In another embodiment, the glenoid joint surface 102 of the glenoid member 101 comprises a concave cross section relative to an anterior-posterior direction of extension. In another embodiment, the glenoid joint surface 102 of the glenoid member 101 comprises a concave cross section relative to a superior-inferior direction of extension and an anterior-posterior direction of extension.

The stabilizing member 800 and the glenoid member 101 can each comprise a material such as cobalt-chrome, titanium, stainless steel, tantalum, polyethylene, silicon, nylon, polyester polymers or a combination thereof. In one embodiment, the glenoid member 101 comprises a different material than the stabilizing member 800, and in another embodiment, the glenoid member 101 and the stabilizing member 800 comprise the same material. In another embodiment, the glenoid member 101 and the stabilizing member 800 each comprise a material having a different stiffness. Further, the stabilizing member 800 can comprise a malleable material.

The stabilizing member 800 and the glenoid member 101 can further comprise a laminated material. The laminated material can comprise at least two materials, such as cobalt-chrome, titanium, stainless steel, tantalum, polyethylene, silicon, nylon and polyester polymers.

In another embodiment, the glenoid member 101 can comprise autologous bone harvested from intra-oral sources of a human patient. For example, the autologous bone can be harvested from an iliac crest of a pelvis.

In another embodiment, the glenoid member 101 can comprise allograft bone harvested from intra-oral sources of a different human patient. For example, the allograft bone can be harvested from an iliac crest of a pelvis.

In another embodiment, the glenoid member 101 can comprise xenograft bone harvested from intra-oral sources of a bovine species or a porcine species.

In addition, the stabilizing member 800 can be constructed and arranged to conform to an anterior or posterior surface of a scapula 110. In one embodiment, the stabilizing member 800 is machined to conform to the contour of a patient's scapula 110. The stabilizing member 800 can be machined according to an X-ray image, CT scan, MRI, Nuclear image, Ultra sound image or combinations thereof.

In an alternative embodiment, one or more extending members, protrude from first arm portion 808 and/or second arm portion 810, such as at the locations of attachment orifices 812a and 812b respectively. These protrusions may be configured to attach to scapula 110 and/or protrude into scapula 110.

FIGS. 10a and 10b are top perspective views of an implantable shoulder prosthesis in accordance with embodiments of the present invention. A shoulder prosthesis 100 can further comprise a glenoid member 101 and first and second stabilizing members 906, 908 attached thereto. In one embodiment, the first and second stabilizing members 906, 908 are attached to an off-center region of the medial face 122 of the glenoid member 101. In another embodiment, the first and second stabilizing members 906, 908 are attached to the medial face 122 of the glenoid member 101 such that a side surface of each of the first and second stabilizing members 906, 908 is aligned with an outer side surface of the glenoid member 101. Further, embodiments can comprise first and second stabilizing members 906, 908 that can be removably attached to the glenoid member 101.

The first and second stabilizing members 906, 908 can comprise a material such as cobalt-chrome, titanium, stainless steel, tantalum, polyethylene, silicon, nylon, polyester polymers, other biocompatible materials, or a combination thereof.

The first and second stabilizing members 906, 908 can further comprise at least one attachment orifice positioned thereon, which is constructed and arranged to receive attachment mechanisms 910a and 910b. When engaged, the attachment mechanisms 910a and 910b operate to secure the first and second stabilizing members 906, 908 to lateral surfaces of a scapula 110.

The attachment mechanisms 910a and 910b can comprise a bone screw, a molly bolt, a machine screw, a rivet or a bolt. The attachment mechanisms 910a and 910b can be further secured by nuts 912a and 912b.

In addition, the attachment mechanisms 910a and 910b and nuts 912a and 912b can comprise a material such as cobalt-chrome, titanium, stainless steel, tantalum, polyethylene, silicone, nylon, polyester polymers, other biocompatible materials, or a combination thereof.

FIG. 11 is top perspective view of an implantable shoulder prosthesis comprising a hinge in accordance with embodiments of the present invention. Shoulder prosthesis 100 can further comprise a glenoid member 101 having a hinge 904, which allows a head portion of a humeral member to dislocate prior to stressing the glenoid member 101 of the implantable shoulder prosthesis 100. The hinge 904 can comprise a material such as rubber, plastic, silicon and the like.

FIGS. 12a, 12b and 12c illustrate a plurality of hinge configurations of the glenoid joint surface of the implantable shoulder prosthesis of FIG. 11 in accordance with embodiments of the present invention.

Referring to FIG. 12a, the glenoid member 101 can comprise a first-fourth portions connected together via a hinge 904. In this embodiment, the hinge 904 comprises a first hinge portion, 904a, that extends in a superior/inferior direction and a second hinge portion 904b that extends in an anterior/posterior direction.

In one embodiment, a torsional stiffness of the first hinge portion is greater than a torsional stiffness of the second hinge portion. In another embodiment, a torsional stiffness of the first hinge portion is less than or equal to a torsional stiffness of the second hinge portion.

Referring to FIG. 12b, the glenoid member 101 can comprise first and second portions connected together via hinge 904b. In this embodiment, the hinge 904b extends in an anterior/posterior direction, allowing the first and second portions of the glenoid member to flex about a longitudinal axis of the hinge 904b.

Referring to FIG. 12c, the glenoid member 101 can comprise first and second portions connected together via a hinge 904a. In this embodiment, the hinge 904a extends in an superior/inferior direction, allowing the first and second portions of the glenoid member to flex about a longitudinal axis of the hinge 904a.

FIGS. 13a and 13b are top perspective views of an implantable shoulder prosthesis in accordance with embodiments of the present invention. A shoulder prosthesis 100 can further comprise a glenoid member 101 and a stabilizing member 800, 906 having a dampener 104. In this embodiment, the dampener 104 positioned along the stabilizing member 800, 906, and is constructed and arranged to absorb a load force 116 applied to the glenoid joint surface 102 of the glenoid member 101 such that a reduced load force is transferred to the attachment mechanisms 910a and 910b and/or the glenoid cavity of a scapula 110. As a result of the dampening of the load force 116, notching and chipping of bone and component loosening associated with the implantable shoulder prosthesis 100 is reduced.

Figure 14:
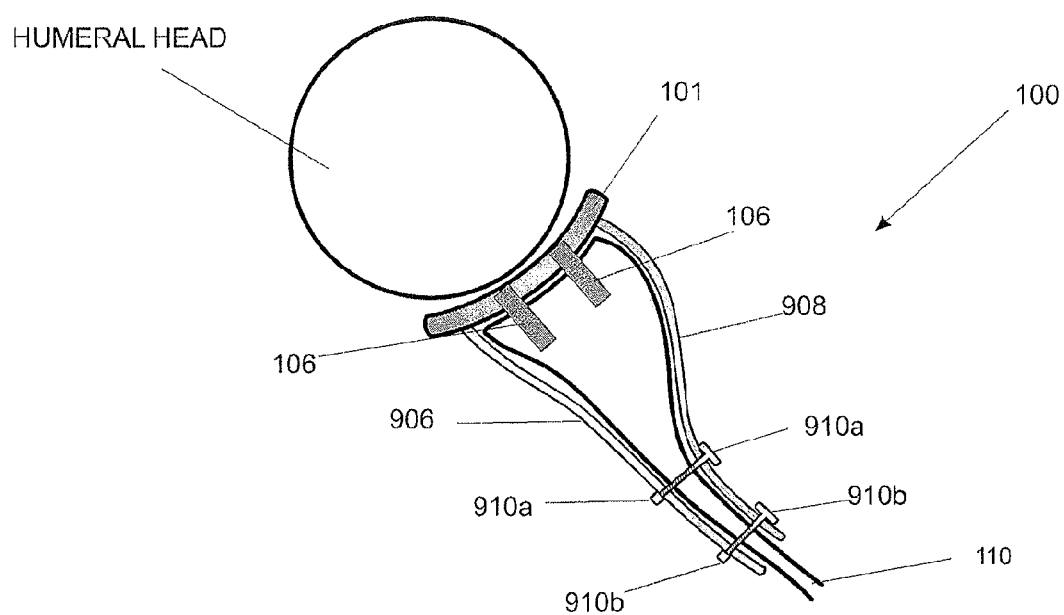
FIG. 14 is a top perspective view of an implantable shoulder prosthesis in accordance with embodiments of the present invention.

FIG. 14 is a top perspective view of an implantable shoulder prosthesis in accordance with embodiments of the present invention. A shoulder prosthesis 100 can further comprise a glenoid member 101, at least one glenoid fixation member 106 and at least one stabilizing member 906, 908. In this embodiment, the glenoid fixation member 106 can be constructed and arranged to attach the glenoid member 101 to a glenoid cavity of a scapula 110 and the attachment mechanisms 910a and/or 910b operate to secure the at least one stabilizing member 906, 908 to a lateral surface of a scapula 110. Glenoid fixation members 106 may comprise pins, screws, fins, keels or other scapular engagement elements.

Figure 15:
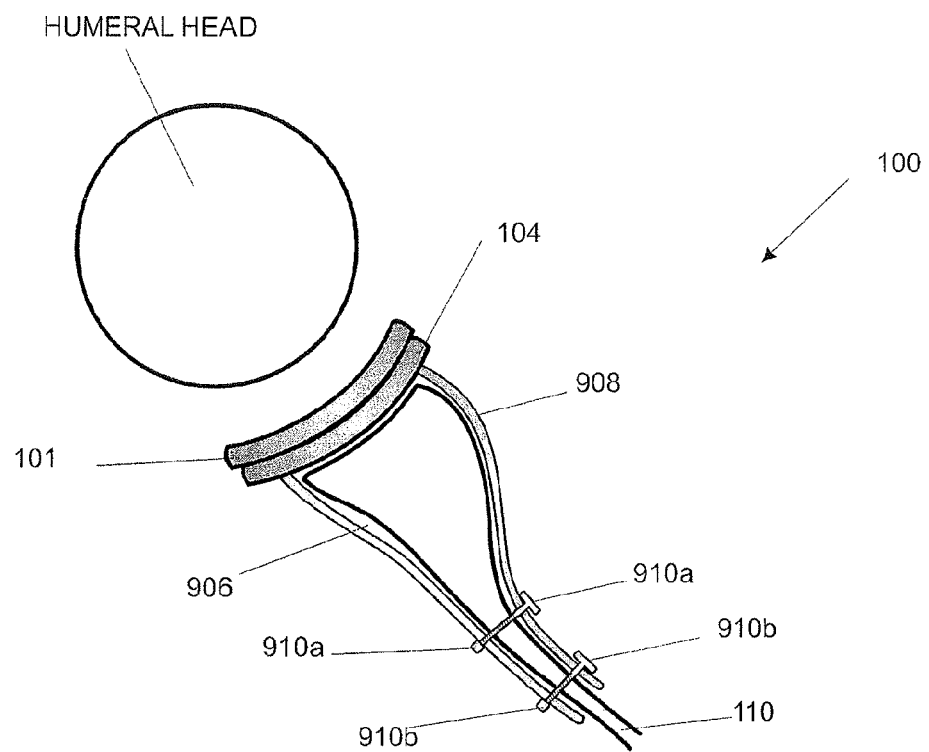
FIG. 15 is a top perspective view of an implantable shoulder prosthesis in accordance with embodiments of the present invention.

FIG. 15 is a top perspective view of an implantable shoulder prosthesis in accordance with embodiments of the present invention. A shoulder prosthesis 100 can further comprise a glenoid member 101, a dampener 104 and first and second stabilizing members 906, 908.

Figure 16:
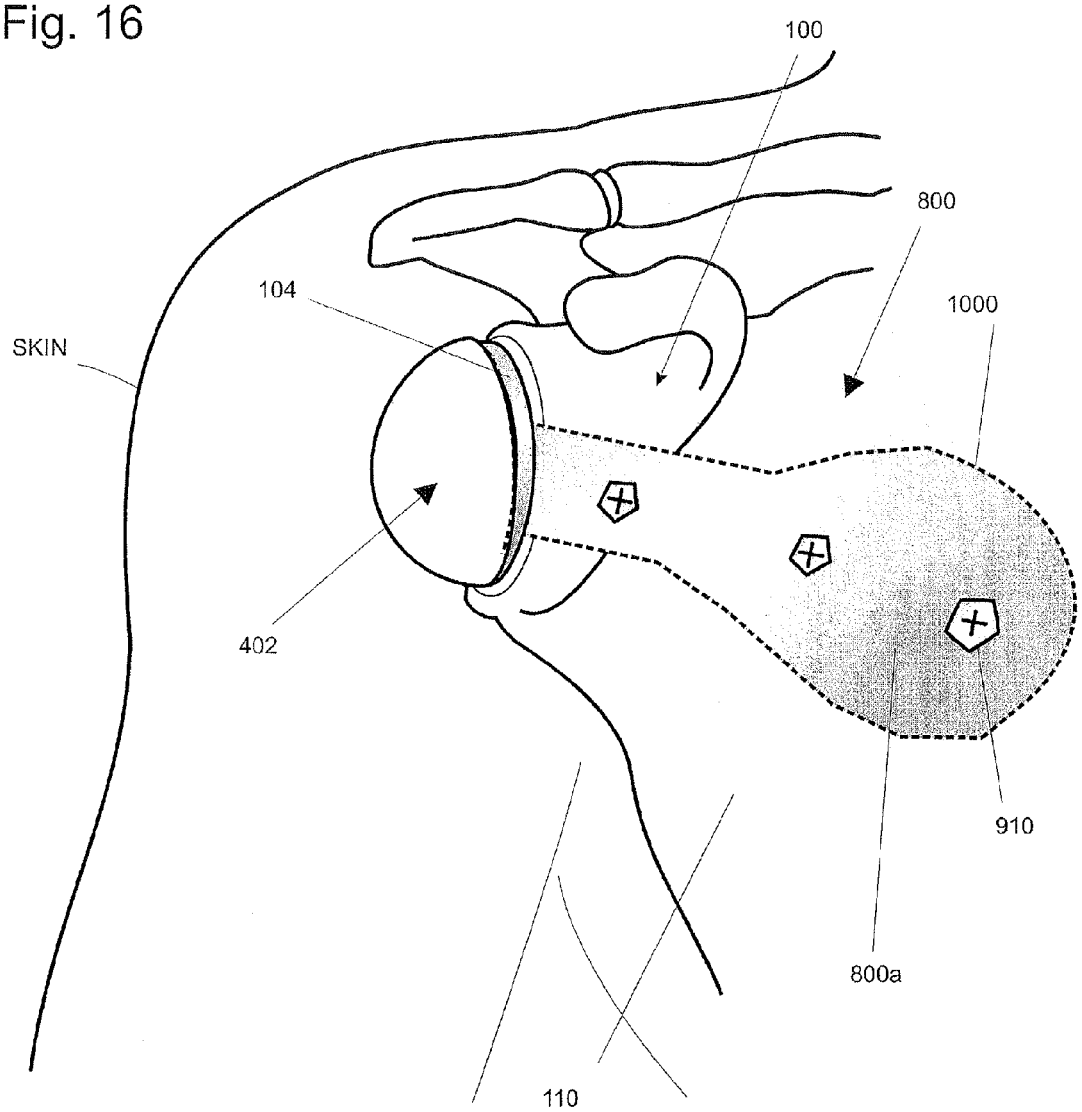
FIG. 16 is an anterior facing environmental view of an implantable shoulder prosthesis in accordance with embodiments of the present invention.

FIG. 16 is an anterior facing environmental view of an implantable shoulder prosthesis in accordance with embodiments of the present invention. A shoulder prosthesis 100 can further comprise a glenoid member 402 with a convex geometry, an optional dampener 104 and a stabilizing member 800 having an enlarged surface 800a. The enlarged surface 800a of the stabilizing member 800 can distribute applied forces such as to prevent the fracture of a scapula bone 110.

Glenoid member 402 can comprise a material such as cobalt-chrome, titanium, stainless steel, tantalum, polyethylene, silicon, nylon, polyester polymers or a combination thereof. In another embodiment, glenoid member 402 can comprise a dampening portion and/or material.

The shoulder prosthesis 100 can further comprise a cushion material 1000 connected to the stabilizing member 800, and positioned between the stabilizing member 800 and a surface of a scapula 110. The cushion material 1000 can comprise a material such as foam, rubber, plastic, silicon and the like.

Figure 17:
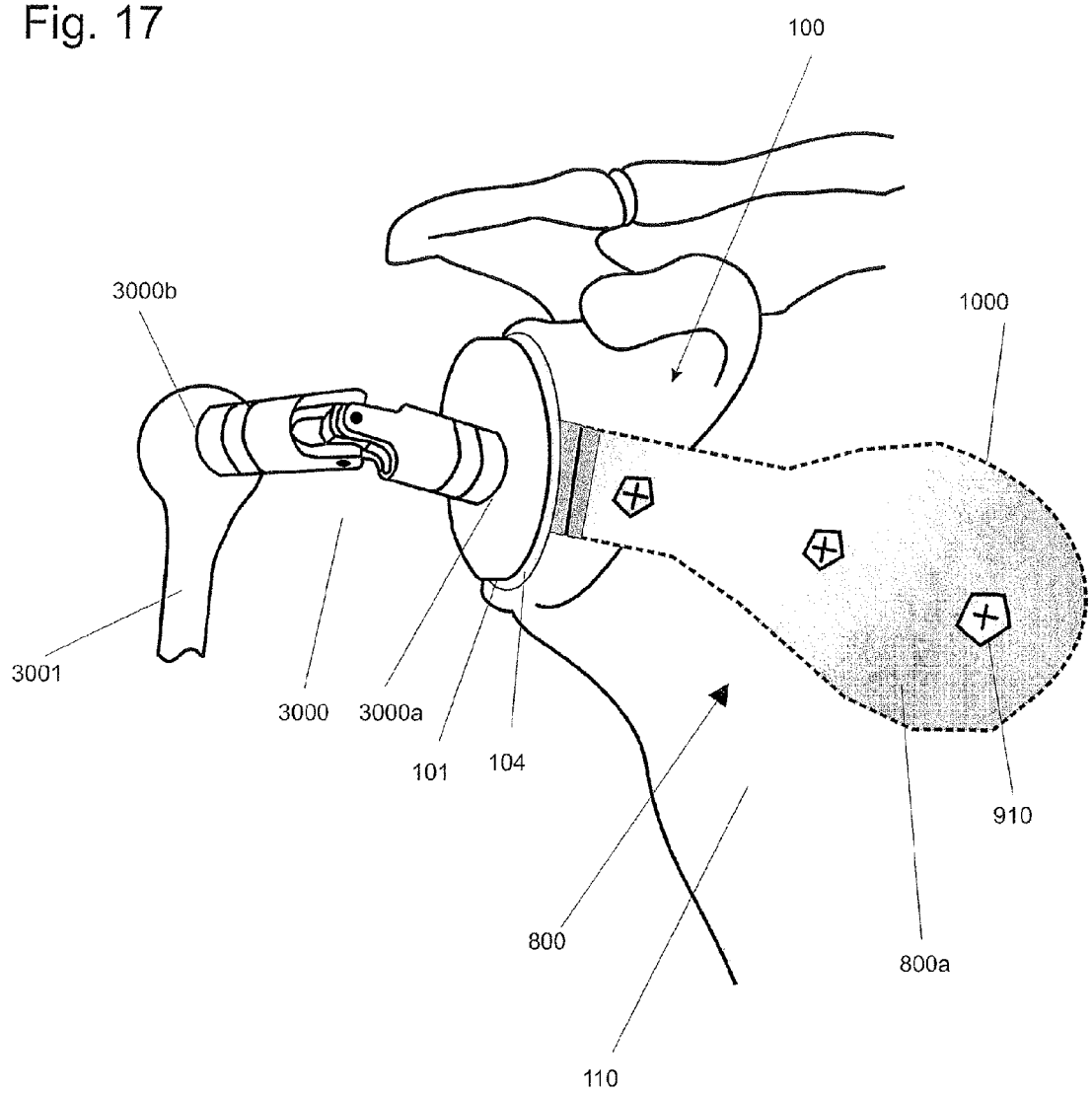
FIG. 17 is an anterior facing environmental view of a constrained implantable shoulder prosthesis comprising a dampener in accordance with embodiments of the present invention.

FIG. 17 is an anterior facing environmental view of a constrained implantable shoulder prosthesis comprising a dampener in accordance with embodiments of the present invention. A shoulder prosthesis 100 can further comprise a glenoid member 101, an optional dampener 104 and a stabilizing member 800 having an enlarged surface 800a. The enlarged surface 800a of the stabilizing member 800 can distribute applied forces such as to prevent the fracture of a scapula bone 110.

Glenoid member 101 can comprise a material such as cobalt-chrome, titanium, stainless steel, tantalum, polyethylene, silicon, nylon, polyester polymers or a combination thereof. In another embodiment, glenoid member 101 can comprise a dampening portion and/or material.

Glenoid member 101 is fixedly attached to a first end 3000a of universal joint 3000. Universal joint 3000 is fixedly attached at a second end 3000b to prosthetic humeral head and stem 3001.

The shoulder prosthesis 100 can further comprise a cushion material 1000 connected to the stabilizing member 800, and positioned between the stabilizing member 800 and a surface of a scapula 110. The cushion material 1000 can comprise a material such as foam, rubber, plastic, silicon and the like.

Figure 18:
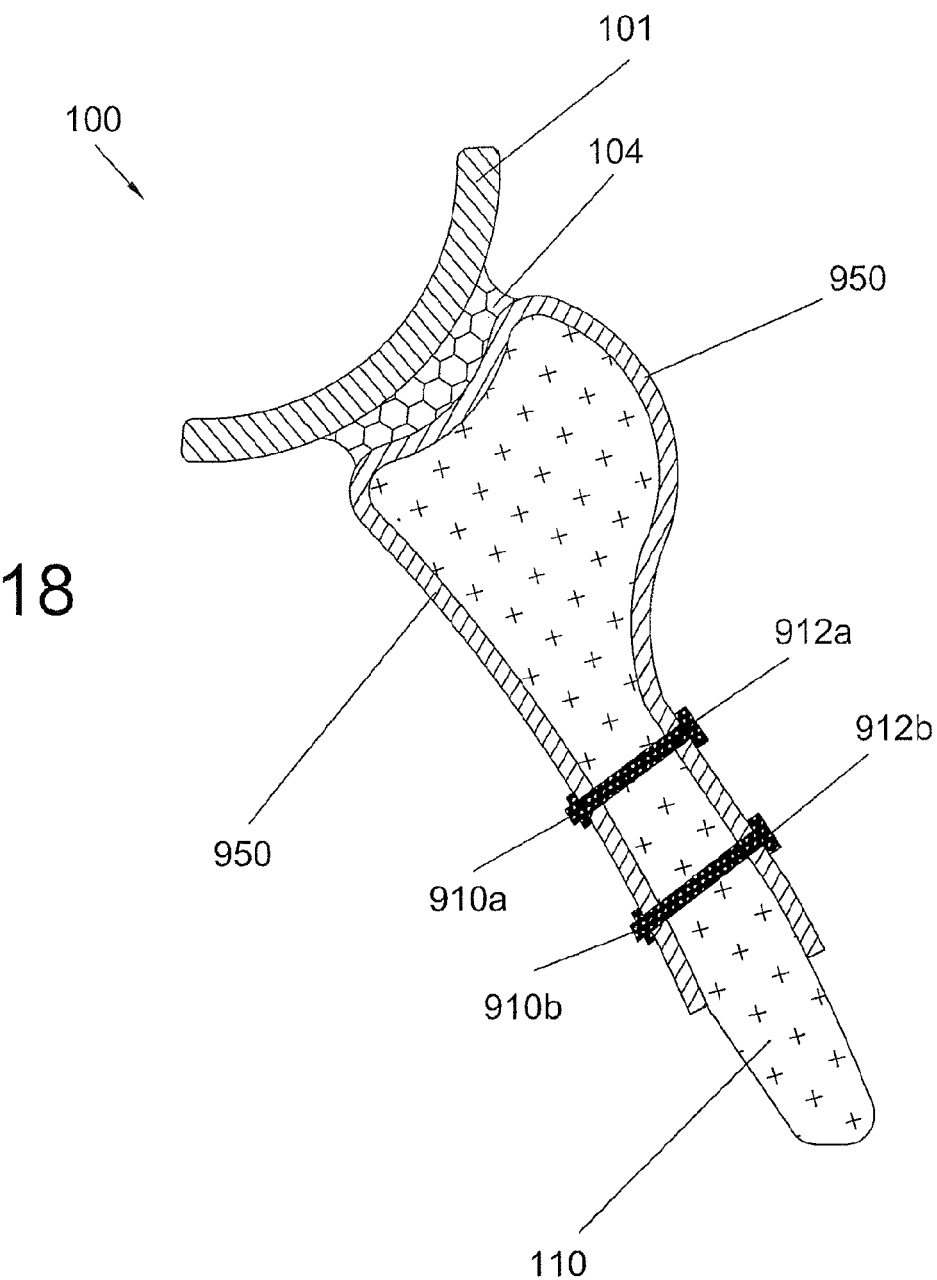
FIG. 18 is a top perspective view of an implantable shoulder prosthesis in accordance with embodiments of the present invention.

FIG. 18 is a top perspective view of an implantable shoulder prosthesis in accordance with embodiments of the present invention. A shoulder prosthesis 100 can further comprise a glenoid member 101, a dampener 104 and a continuous scapular fixation member 950.

In this embodiment, the dampener 104 is positioned between the glenoid member 101 and the scapular fixation member 950. Dampener 104 may comprise a foam or other cellular material with a rigidity constructed and arranged to allow glenoid member 101 to deflect under high loads, such as to prevent dislocation of a natural or artificial humeral head, and or prevent damage to scapula 110. The scapular fixation member 950 is constructed and arranged to conform to surfaces of a scapula 110. Such surfaces can include an anterior surface, a posterior surface and a glenoid surface of a scapula 110.

Figure 19:
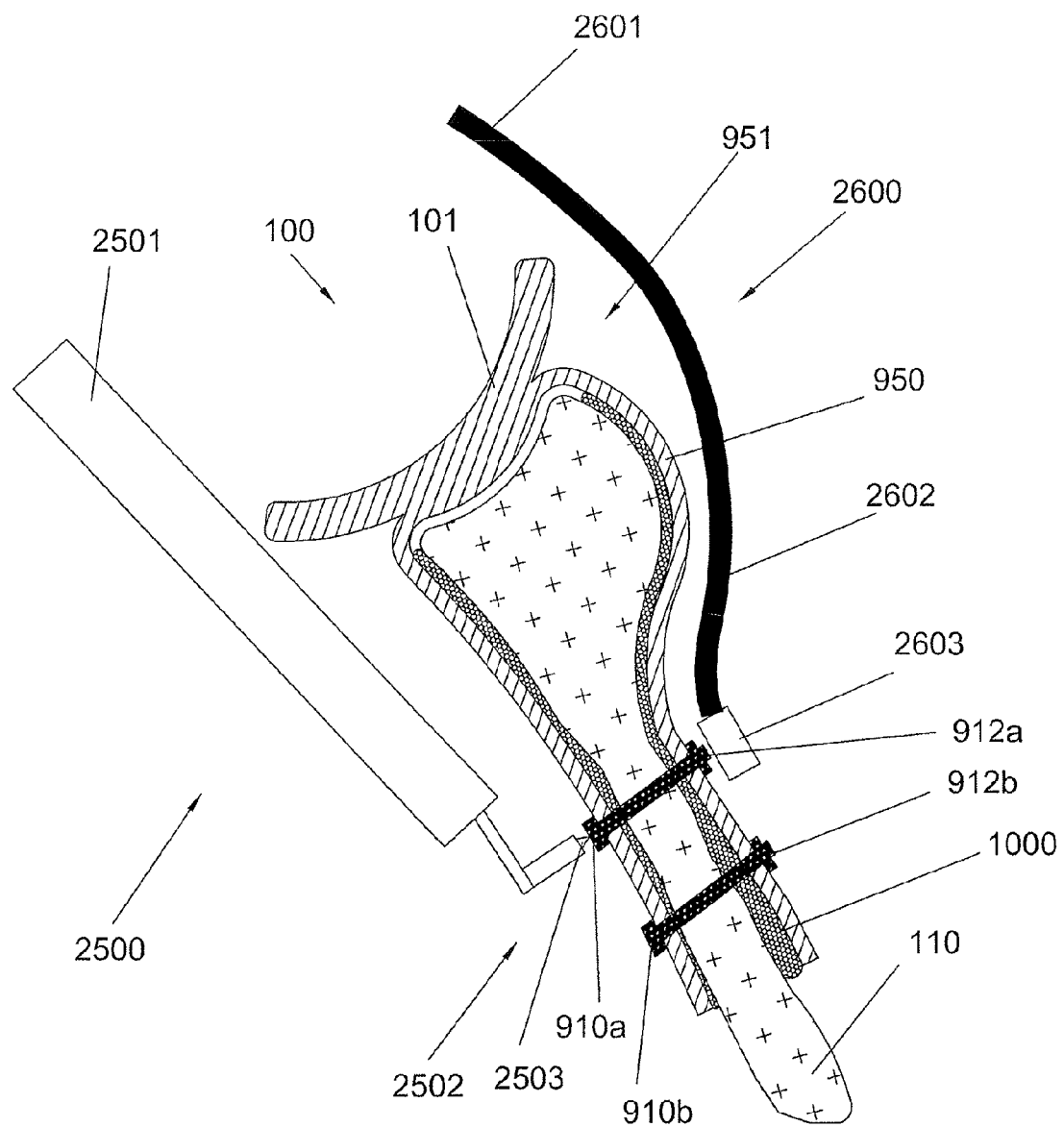
FIG. 19 is a top perspective view of an implantable shoulder prosthesis and surgical tools for implanting the shoulder prosthesis in accordance with embodiments of the present invention.

FIG. 19 is a top perspective view of an implantable shoulder prosthesis and surgical tools for implanting the shoulder prosthesis in accordance with embodiments of the present invention. A shoulder prosthesis 100 can further comprise a glenoid assembly 951 comprising a glenoid member 101, a scapular fixation member 950 and a cushion material 1000.

The cushion material 1000 is positioned between the scapula fixation member 950 and surfaces of a scapula 110, such that the shoulder prosthesis 100 conforms to the contour of the scapula 110.

Also shown in FIG. 19 is tool 2500 comprising handle 2501, ratchet assembly 2502 and engaging tip 2503. Tool 2500 is constructed and arranged such that rotation of handle 2501 causes ratchet assembly 2502 and tip 2503 to rotate. Tip 2503, such as a Phillips, torx, hex or other fastener engaging tip is configured to engage the head of attachment mechanism 910a and/or 910b.

Also shown in FIG. 19 is tool 2600 comprising handle 2601, shaft 2602 and wrench end 2603. In a preferred embodiment, shaft 2602 is malleable such as to be shaped by a clinician during a surgical implantation procedure. Wrench end 2603 is configured to engage nut 912a and/or 912b such that rotation of attachment mechanism 910a and/or 910b, respectively, prevents rotation of nut 912a and/or 912b. In an alternative embodiment, wrench end 2603 may be constructed and arranged to rotate, such as via rotation of handle 2601. In another alternative embodiment, tool 2500 and/or tool 2600 may include torque or other force measurement feedback such as to tighten attachment mechanisms 910a and/or 910b to nuts 912a and/or 912b, respectively, at a desired level of compression.

Figure 20:
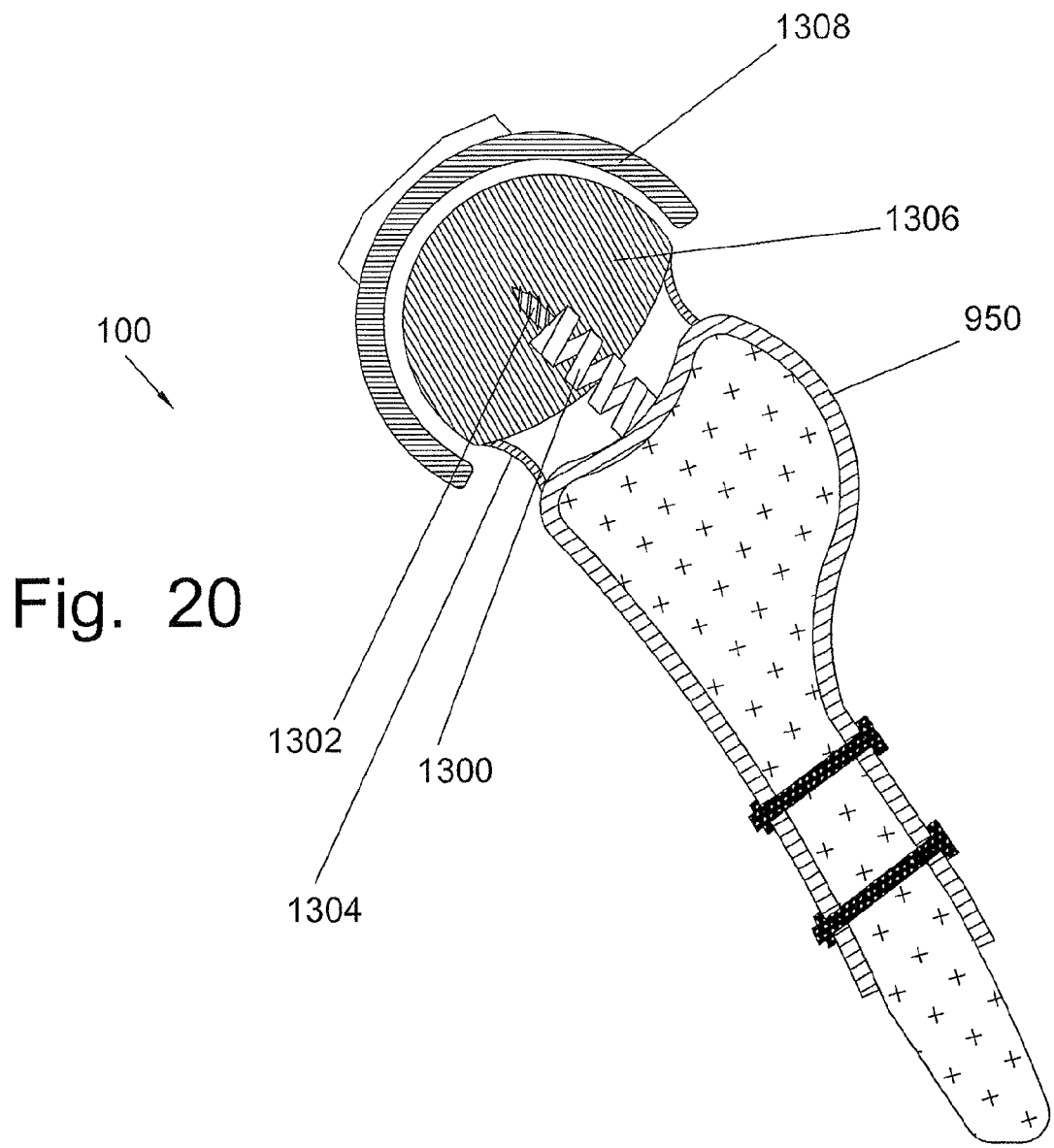
FIG. 20 is a top perspective view of a constrained implantable shoulder prosthesis in accordance with embodiments of the present invention.

FIG. 20 is a top perspective view of a constrained implantable shoulder prosthesis in accordance with embodiments of the present invention. A shoulder prosthesis 100 can further comprise a constrained humeral cup 1308 that is constructed and arranged to interface with an convex glenoid portion 1306.

Glenoid portion 1306 is attached to a scapular fixation member 950 by a screw 1302 and a flexible membrane 1304. The flexible membrane 1304 can comprise a compressible material, for example, a rubber compound, plastic compound, a foam material, a silicon material and the like, and is constructed and arranged to absorb and dissipate a load force 116 that is applied to the artificial humeral head 1306. In addition, the screw 1302 can comprise a spring 1300 to further absorb and dissipate a load force 116 that is applied to the artificial humeral head 1306.

The constrained humeral cup 1308 is constructed and arranged to limit movement of a humeral member. For example, the humeral cup 1308 can limit movement of humeral member in at least two directions. In one embodiment, humeral cup 1308 surrounds greater than 180 degrees of the glenoid portion 1306. In an alternative embodiment, one or both ends of cup 1308 are constructed of bioabsorbable material such that the constraint is time limited. Duration of constraint may be selected to allow healing or other physiologic processes to occur prior to full motion enabling of the patient's shoulder joint. Typical duration times include periods greater than one week, greater than one month, greater than 3 months and greater than 6 months.

Figure 21:
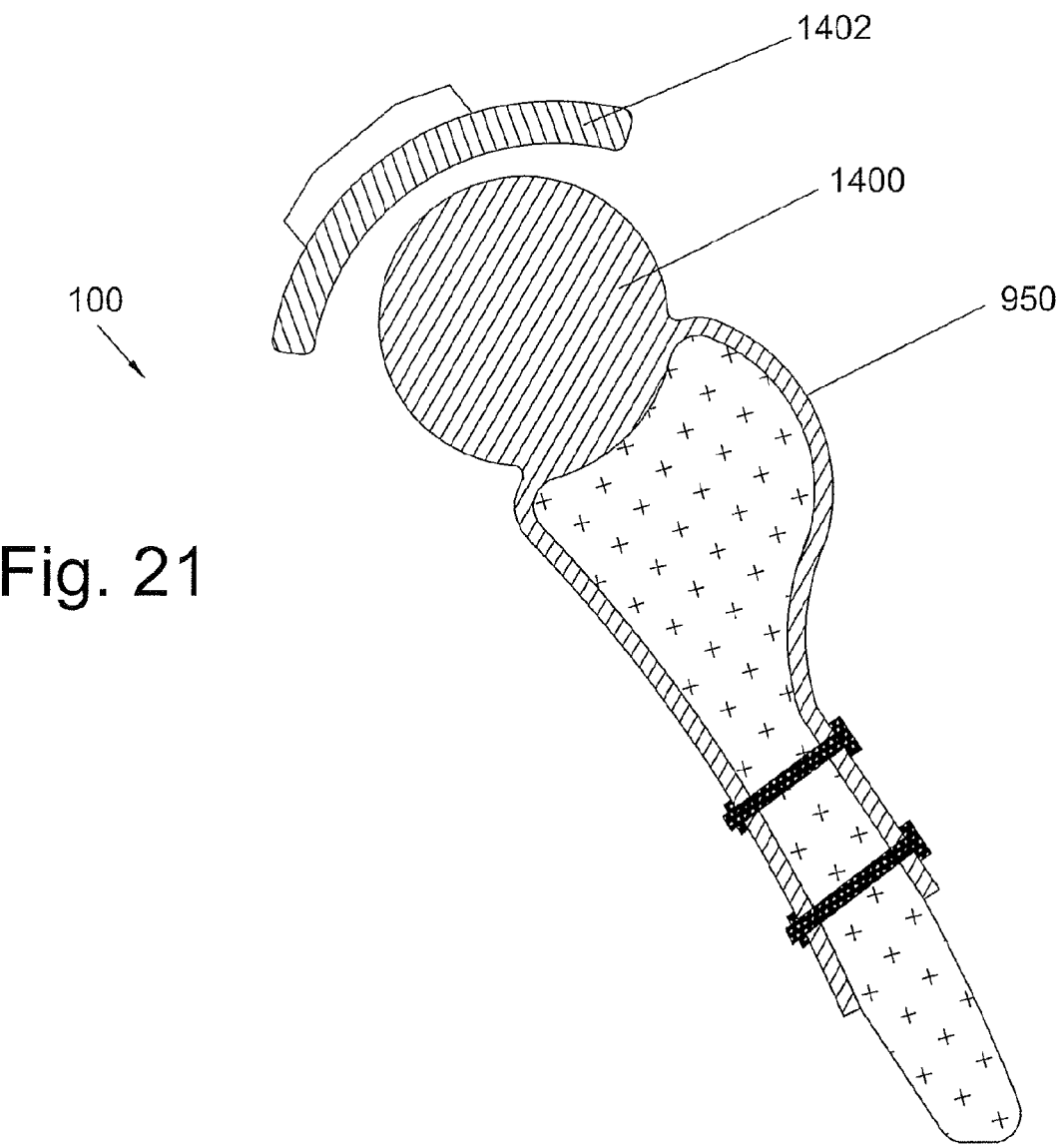
FIG. 21 is a top perspective view of an implantable shoulder prosthesis in accordance with embodiments of the present invention.

FIG. 21 is a top perspective view of an implantable shoulder prosthesis in accordance with embodiments of the present invention. A shoulder prosthesis 100 can further comprise a concave humeral cup 1402 that is constructed and arranged to interface with an convex glenoid portion 1400. In this embodiment, glenoid portion 1400 is integral with the scapular fixation member 950.

Figure 22A:
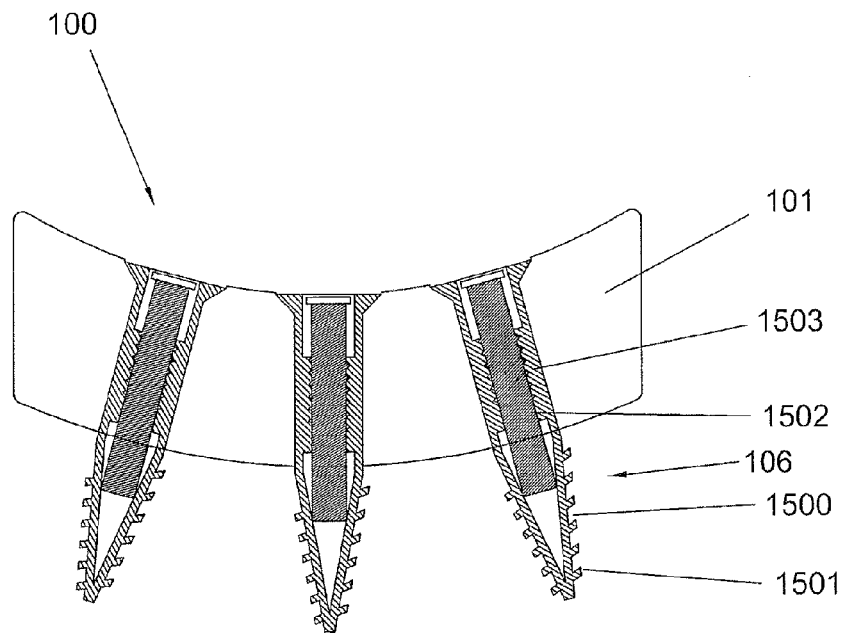
FIGS. 22a and 22b are cross-sectional views of a glenoid member having expandable glenoid fixation members in accordance with embodiments of the present invention.
Figure 22B:
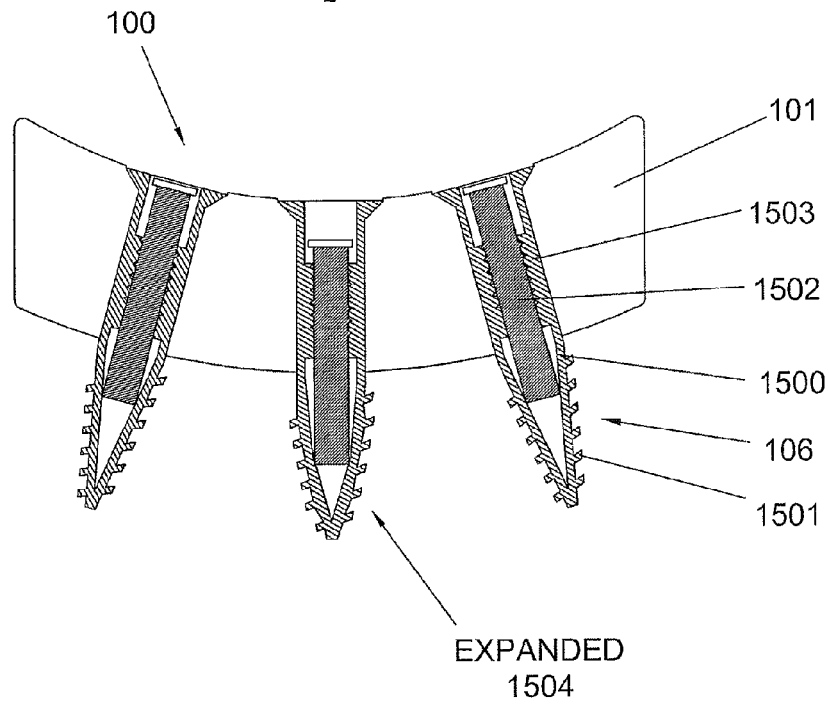

FIGS. 22a and 22b are cross-sectional views of a glenoid member 101 having expandable glenoid fixation members in accordance with embodiments of the present invention. A shoulder prosthesis 100 can further comprise a glenoid member 101 having a plurality of glenoid fixation members 106 that are expandable.

An expandable glenoid fixation member 106 comprises an outer screw portion 1500 and an inner expanding post 1502. The outer screw portion 1500 comprises threads 1501 for penetrating human bone, such as, a scapula 110. The inner screw portion 1502 comprises threads 1503, such that rotational movement of the inner screw portion 1502 operates to advance or retract the inner screw portion 1502 within the outer screw portion 1500.

Referring to FIG. 22b, the advancement of the inner screw portion 1502 within the outer screw portion 1500 controls the expansion of the outer screw portion 1500. For example, when the inner screw portion 1502 is advanced within the outer screw portion 1500, an expanded portion 1504 of the outer screw portion 1500 is formed.

In this embodiment, the expansion of the outer screw portion 1500, as shown in the middle fixation member 106, can tighten a glenoid fixation member 106 that has become loose and/or prevent initial loosening.

FIGS. 23a, 23b, 23c and 23d are cross-sectional views of a glenoid member having expandable glenoid fixation members in accordance with embodiments of the present invention. A shoulder prosthesis can further comprise a glenoid member 101 and an expandable glenoid fixation member 106.

Figure 23A:
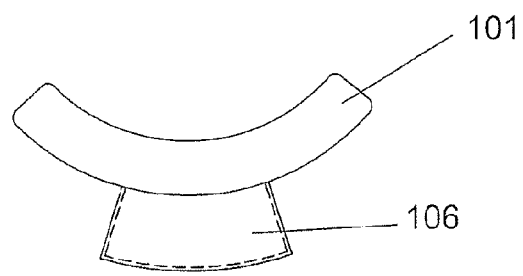
FIGS. 23a, 23b, 23c and 23d are cross-sectional views of a glenoid member having expandable glenoid fixation members in accordance with embodiments of the present invention.
Figure 23B:
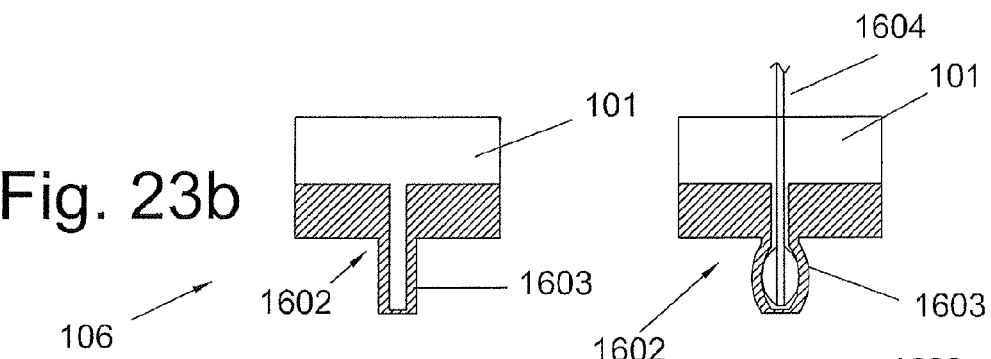

Referring to FIG. 23b, an expandable glenoid fixation member 106 can comprise a fin-type member 1602 having an expandable portion 1603. A balloon tool 1604 can be used to expand the fin-type member 1602, such as by expansion of a balloon portion with a fluid. Alternatively or additionally, tool 1604 may comprise an expandable cage, such as a nitinol cage expanded with heat, or an assembly that expands due to applied magnetic forces.

Figure 23C:
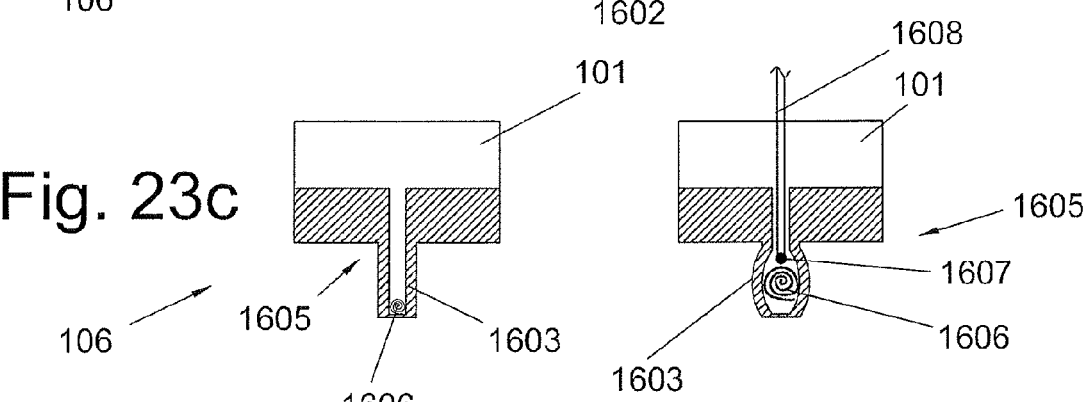

Referring to FIG. 23c, an expandable glenoid fixation member 106 can comprise a fin-type member 1605 having a Nitinol coil 1606 positioned within an expandable portion 1603. A heated tip 1607 of a heating tool 1608 can be used to expand the Nitinol coil 1606 which in turn expands portion 1603.

Figure 23D:
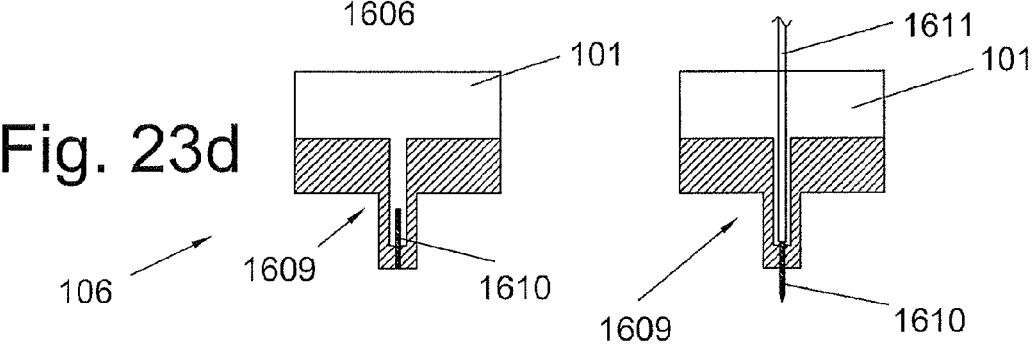

Referring to FIG. 23d, an expandable glenoid fixation member 106 can comprise a fin-type member 1609 having a sharp pin 1610. A tool 1611, such as a rigid shaft, can be used to extend the sharp pin 1610 outwardly from the fin-type member 1609.

Figure 24:
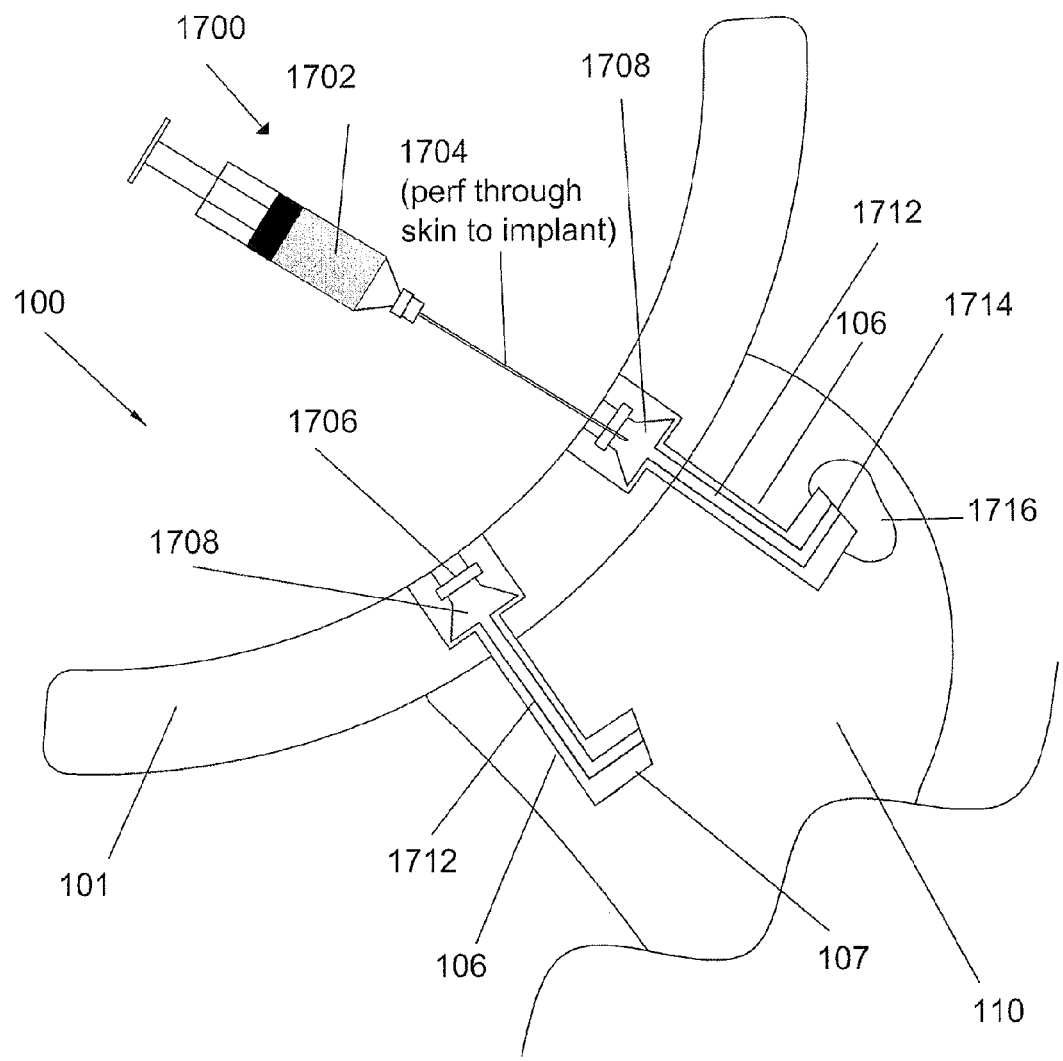
FIG. 24 is a top perspective view of an implantable shoulder prosthesis comprising a plurality of glenoid fixation members each having an access port through which an adhesive material can be added in accordance with embodiments of the present invention.

FIG. 24 is a top perspective view of an implantable shoulder prosthesis comprising a plurality of glenoid fixation members each having an access port through which material such as an adhesive material can be added in accordance with embodiments of the present invention. A shoulder prosthesis 100 can comprise a glenoid member 101 and a plurality of glenoid fixation members 106 each having an access port or adhesive inlet through which an adhesive material can be added. The access port or adhesive inlet of the glenoid fixation members 106 can comprise a resealable septum 1706, which can be connected inline with a chamber 1708 and a transport tube 1712.

After implantation of the shoulder prosthesis 100, a cavity 1716 can form in the glenoid region of a scapula 110 as a result of various types of load forces exerted on glenoid member 101. As a result of one or more cavities 1716, notching and chipping of scapula bone and/or loosening of the glenoid member 101 may occur. To prevent further damage to or loosening of the shoulder prosthesis 100 and surrounding glenoid area of the scapula 110, a fill material 1702 can be injected, via a syringe 1700 into the cavity 1716 formed in the scapula 110. Fill material 1702 may comprise a cement such as orthopedic bone cement, a glue material, an elastomeric material, a gel foam, a suture material, a nitinol filament, and/or other biocompatible, injectable material. In one embodiment, a needle 1704 of the syringe 1700 is used to pierce the resealable septum 1706. Once pierced, the adhesive material 1702 can be injected into the chamber 1708, through a transport tube 1712 of the glenoid fixation member 106, and out of an output port 1714 into the cavity 1716. As a result, the notching and chipping of scapula bone and/or loosening of the glenoid member 101 can be prevented.

In one embodiment, the resealable septum 1706 is constructed and arranged to be accessed percutaneously. In another embodiment, the resealable septum 1706 is constructed and arranged to be accessed in a minimally invasive procedure. In another embodiment, the resealable septum 1706 is constructed and arranged to be accessed in an open surgical procedure.

Glenoid fixation members 106 may comprise a rotatable anchor 107 configured to engage the scapula 110 when fixation member 106 is rotated; however, other types glenoid fixation members 106 may be used to attach the glenoid member 101 to a scapula 110. For example, a screw, pin, keel or other projection may include an access port or adhesive inlet through which an adhesive or other fill material can be injected.

Figure 25A:
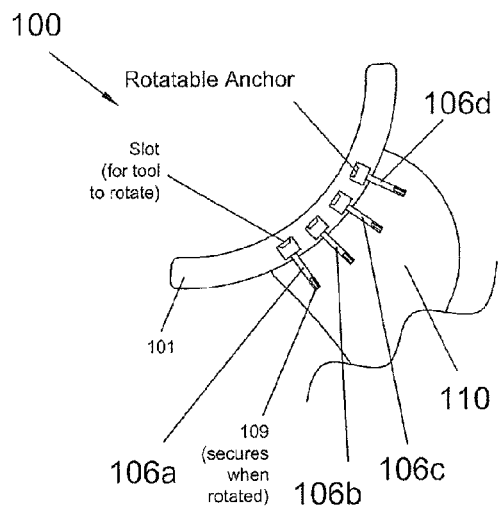
FIGS. 25a, 25b and 25c are top perspective views of an implantable shoulder prosthesis comprising a plurality of glenoid fixation members in which subsets of the plurality of glenoid fixation members are engaged during separate procedures in accordance with embodiments of the present invention.
Figure 25B:
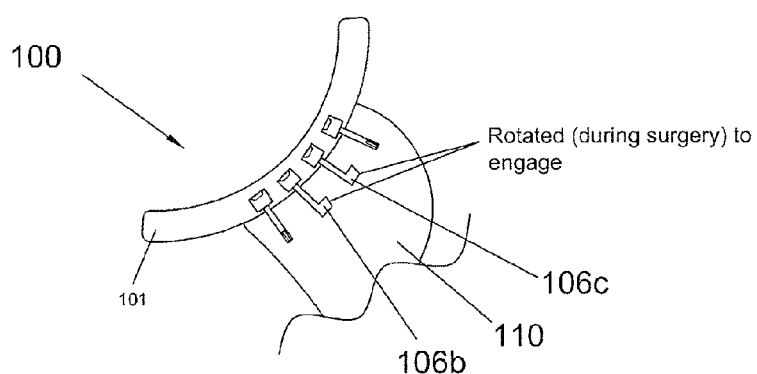
Figure 25C:
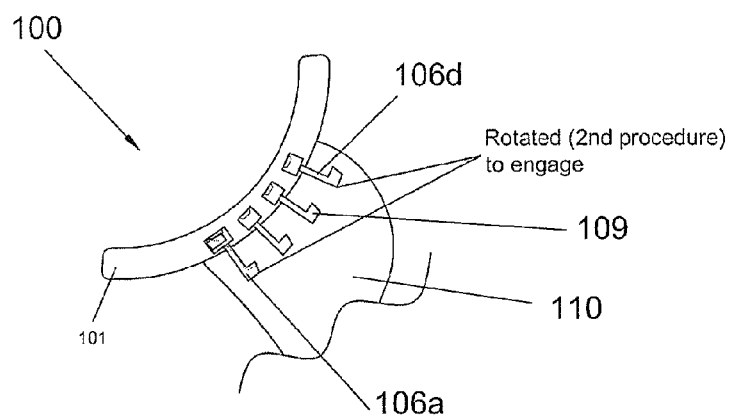

FIGS. 25a, 25b and 25c are top perspective views of an implantable shoulder prosthesis comprising a plurality of glenoid fixation members in which subsets of the plurality of glenoid fixation members are engaged during separate procedures in accordance with embodiments of the present invention. A shoulder prosthesis 100 can comprise a glenoid member 101 and a plurality of glenoid fixation members 106. For example, the shoulder prosthesis can comprise a first glenoid fixation member 106a, a second glenoid fixation member 106b, and third glenoid fixation member 106c, and a fourth glenoid fixation member 106d. In this embodiment, the glenoid fixation members 106 (e.g., first-fourth glenoid fixation members 106a/106b/106c/106d) comprise rotatable engagement anchors; however, other glenoid types of glenoid fixation members 106 can be used to attach the glenoid member 101 to a scapula 110.

In one embodiment, the rotatable engagement anchors can comprise engageable (e.g. comprising a slot for rotation with a screwdriver) securing portions 109 for attaching the glenoid member 101 to a glenoid cavity of a scapula 110. Further, the engageable securing portions can be engaged in response to a magnetic field.

Referring to FIG. 25a, the glenoid member 101 is shown having a complete set of glenoid fixation members 106a/106b/106c/106d implanted in a scapula 110. In this embodiment, the complete set glenoid fixation members 106a/106b/106c/106d are shown un-engaged.

Referring to FIG. 25b, a first subset of glenoid fixation members 106b and 106c are shown engaged, securing the glenoid member 101 to a glenoid cavity of a scapula 110.

Referring to FIG. 25c, the remaining glenoid fixation members 106a and 106d are shown engaged, further securing the glenoid member 101 to a glenoid cavity of a scapula 110. The complete set of engaged glenoid fixation members 106a/106b/106c/106d is shown.

In one embodiment, the first subset of glenoid fixation members 106b and 106c or a portion thereof is engaged, securing the glenoid member 101 to a glenoid cavity of a scapula 110 via securing portion 109 in a first operation or procedure. Subsequently, if the glenoid member 101 becomes loose subsequent to the first operation or procedure, the remaining glenoid fixation members 106a and 106d or a portion thereof, can be engaged via securing portion 109, thus re-securing the glenoid member 101 to a glenoid cavity of a scapula 110. For example, in a second operation or procedure, at least 24 hours after the engagement of the first subset of glenoid fixation members 106b and 106c or a portion thereof, the remaining glenoid fixation members 106a and 106d or a portion thereof is engaged.

In one embodiment, the remaining glenoid fixation members 106a and 106d or a portion thereof can be accessed and engaged percutaneously. In another embodiment, the remaining glenoid fixation members 106a and 106d or a portion thereof can be accessed and engaged in a minimally invasive procedure. In another embodiment, the remaining glenoid fixation members 106a and 106d or a portion thereof can be accessed and engaged in an open surgical procedure.

Figure 26:
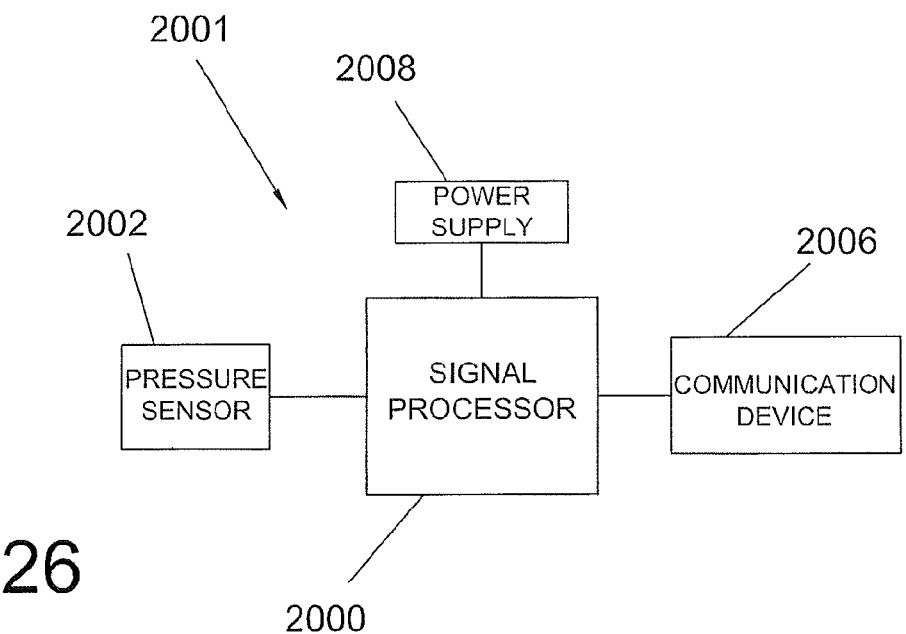
FIG. 26 is a block diagram of a pressure sensing system in accordance with embodiments of the present invention.

FIG. 26 is a block diagram of a pressure sensing system in accordance with embodiments of the present invention. A pressure sensing system 2001 can comprise signal processor 2000, such as, a microprocessor, a digital signal processor, and the like, at least one pressure sensor 2002, an optional biasing element (such as biasing element 2004 of FIG. 28), a communication device 2006 and a power supply 2008.

In some embodiments, the signal processor 2000 comprises data storage elements, such as, non-volatile and volatile memory. In addition, in other embodiments, the pressure sensing system 2001 can further comprises external data storage elements (not shown), such as, non-volatile and volatile memory, which are connected to the signal processor 2000.

The pressure sensor 2002, or a plurality thereof, are electrically connected to the signal processor 2000. The signal processor 2000 receives pressure information in the form of analog or digital signals from the pressure sensor 2002, and as a result, determines if the measured pressure is above, below or equal to a predetermined threshold value stored in system memory.

The power supply 2008 is electrically connected to the pressure sensing system 2001, and supplies electrical energy thereto. In one embodiment, the power supply 2008 comprises one or more rechargeable batteries of the following types or a combination thereof: Lead-acid, Alkaline, Ni-iron, Ni-cadmium, NIH2, NiMH, Ni-zinc, Li ion, Li polymer, Li sulfur[8], Li titanate, Thin film Li, ZnBr, or Silver zinc. In other embodiments, the power supply comprises one or more single-use type batteries.

The communication device 2006 is electrically connected to the signal processor 2000. The communication device 2006 can be used to program, initialized, reset, or adjust the pressure sensing system 2001. In one operating mode, the communication device 2006 receives program data and initialization data from an external device.

In another operating mode, the communication device 2006 transmits stored pressure information (e.g., data). For example, the communication device can be configured to generate a pressure sensor signal corresponding to a pressure measured between the medial face 122 of the glenoid member 101 and a glenoid cavity of a scapula 110. Sensing system 2001 may comprise wireless telemetry, such as information transferred via electromagnetic waves such as radiofrequency waves, light such as infrared light, or other wireless means which transmit information to an external receiver, such as a computer, cellular telephone or the like.

The communication device 2006 can comprise a wireless communication device for transmitting the pressure information or pressure sensor signal. The wireless communication device can operate on a frequency band selected from the group consisting of: 30-300 kHz, 300-3000 kHz, 3-30 MHz, 30-300 MHz, 300-3000 MHz, 3-30 GHz and 30-300 GHz.

Figure 28:
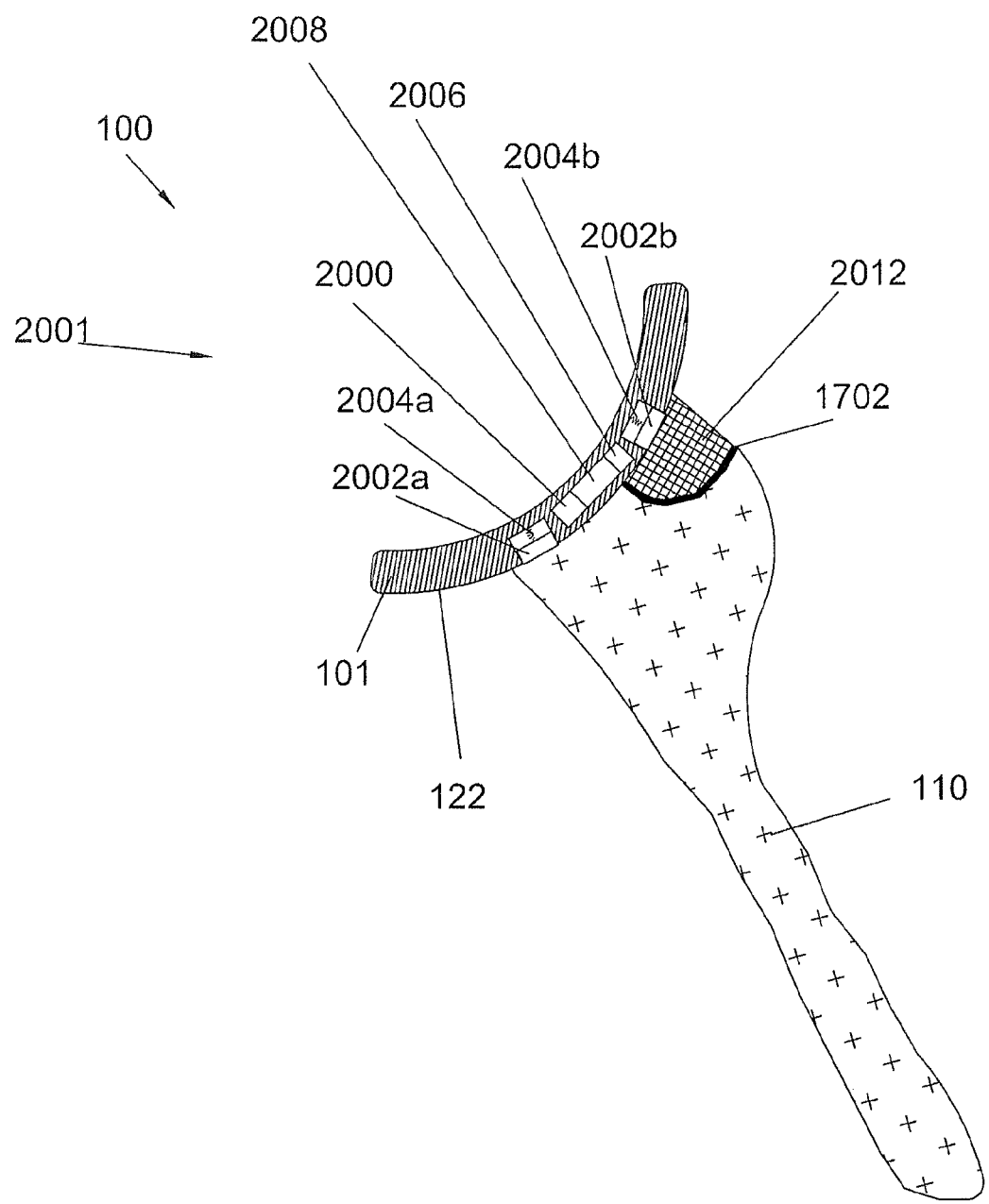
FIG. 28 is a top perspective view of an implantable shoulder prosthesis comprising a pressure sensing system in accordance with embodiments of the present invention.

FIG. 28 is a top perspective view of an implantable shoulder prosthesis comprising a pressure sensing system in accordance with embodiments of the present invention. An implantable shoulder prosthesis 100 can comprise a glenoid member 101 and pressure sensing system 2001.

In one embodiment, the signal processor 2000, the communication device 2006 and the power supply 2008 are encapsulated within the glenoid member 101. In other embodiments, the signal processor 2000, the communication device 2006 and the power supply 2008 of the pressure sensing system 2001 are partially formed in the glenoid member 101.

The pressure sensing system 2001 optionally comprises biasing elements 2004a and 2004b that bias the pressure sensors 2002a and 2002b in an outward direction, away from the medial face 122 of the glenoid member 101. The biasing element 2004 can comprise a spring, a rubber plug, a foam plug, a silicon plug, a plastic plug or a combination thereof.

In the case of a deformed scapula 110, a bulker 2012 can be secured to a deformed portion of a scapula 110 by a fill material, such that an implantable prosthesis 100 can be securely attached to the scapula, such as to prevent rocking.

In one embodiment, fill material 1702 is selected from the group consisting of: glue or other adhesive material; cement such as orthopedic bone cement, gel foam, fill material including one or more bone grafts, elastomeric material; and combinations of these.

The methods disclosed herein can be implemented by the pressure sensing systems 2001 of FIGS. 26 and 28, or equivalent systems, executing a unique set of instructions stored in system memory. As will be appreciated by those skilled in the art, a unique set of instructions can be implemented or embodied in software, firmware, or a combination thereof.

Figure 27:
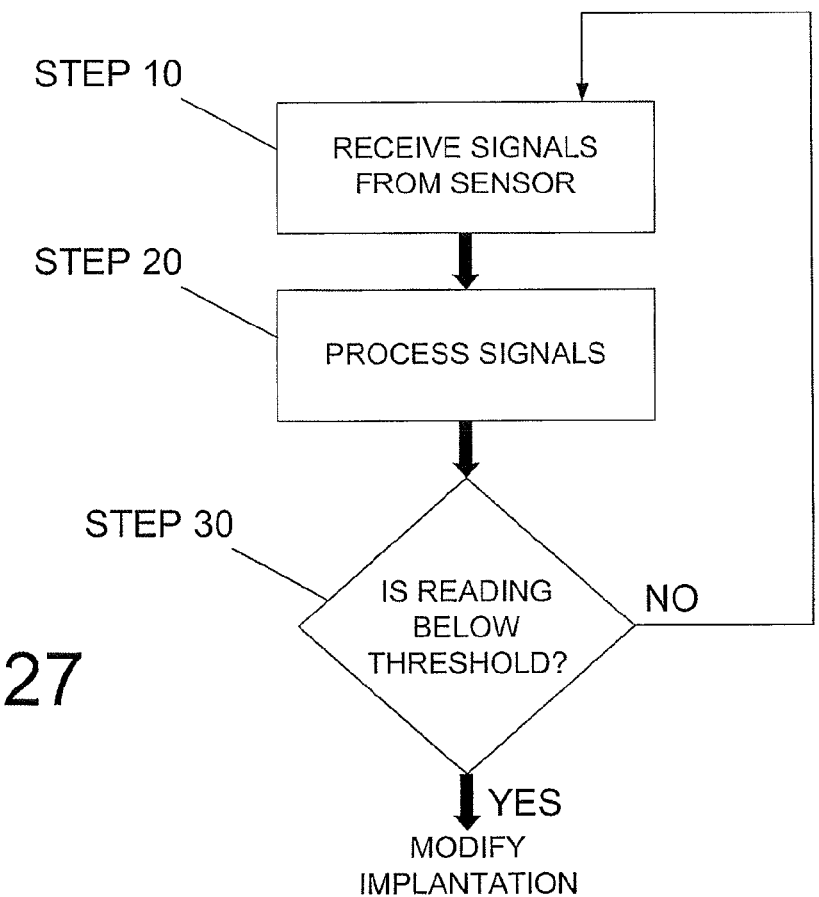
FIG. 27 is a flow diagram illustrating a method of operating a pressure sensing system in accordance with embodiments of the present invention.

FIG. 27 is a flow diagram illustrating a method of operating a pressure sensing system in accordance with embodiments of the present invention. A pressure sensing system, such as the pressure sensor system 2001 of FIG. 26 or 28, is powered on and initialized to execute a unique set of instructions. In one embodiment, the unique set of instructions correspond to the method of operation disclosed in FIG. 27.

The signal processor 2000 of the pressure sensing system 2001 receives pressure information in the form of analog or digital signals from the pressure sensor 2002 (10). The signal processor 2002 converts/processes the received signal to digital form if necessary (20), and determines if the measured pressure is above, below or equal to a predetermined threshold value stored in system memory (30). If the measured pressure is above the predetermined threshold, the pressure sensing system continues to receive and process pressure information from the pressure sensor 2002 (10/20). If the measured pressure is equal to or below the predetermined threshold, a modification signal is generated by the signal processor 2000 indicating that the glenoid member 101 may be loose.

Furthermore, the pressure sensing system 2001 may store the received pressure information received from the pressure sensor 2002 for each iteration in system memory. This stored information, can be later accessed via the communication device 2006.

Figure 29:
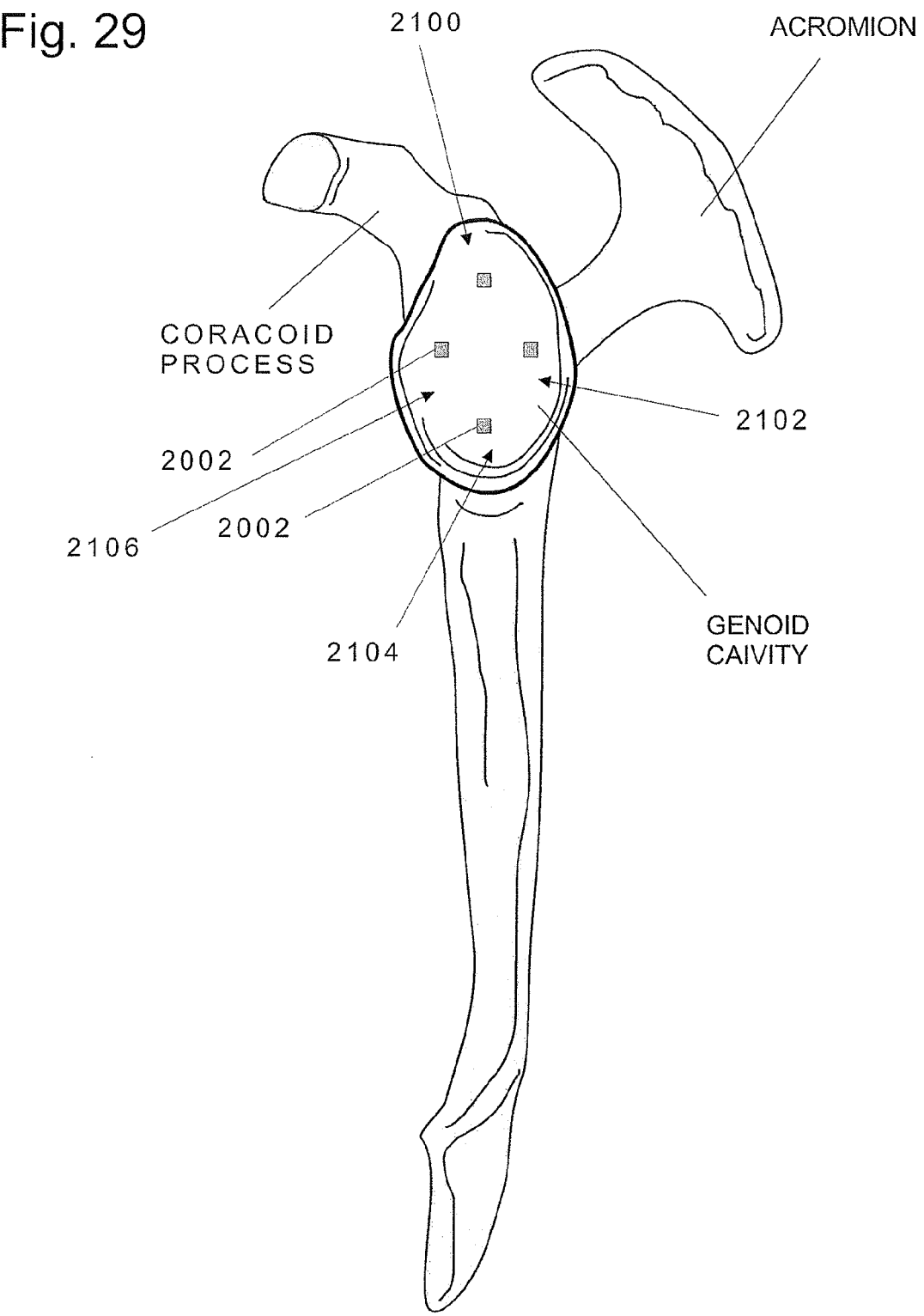
FIG. 29 is a lateral/medial facing view of a scapula illustrating pressure sensor locations in accordance with embodiments of the present invention.

FIG. 29 is a lateral/medial facing view of a scapula illustrating pressure sensor locations in accordance with embodiments of the present invention. The implantable shoulder prosthesis 100 comprising the pressure sensing system 2001 as illustrated in FIG. 26 can be constructed and arranged so that one or more pressure sensors 2002 monitor the pressure at least one of four glenoid cavity locations, which correspond to an upper glenoid cavity location 2100, a right glenoid cavity location 2102, and lower glenoid cavity location 2104 and a left glenoid cavity location 2106.

Figure 30:
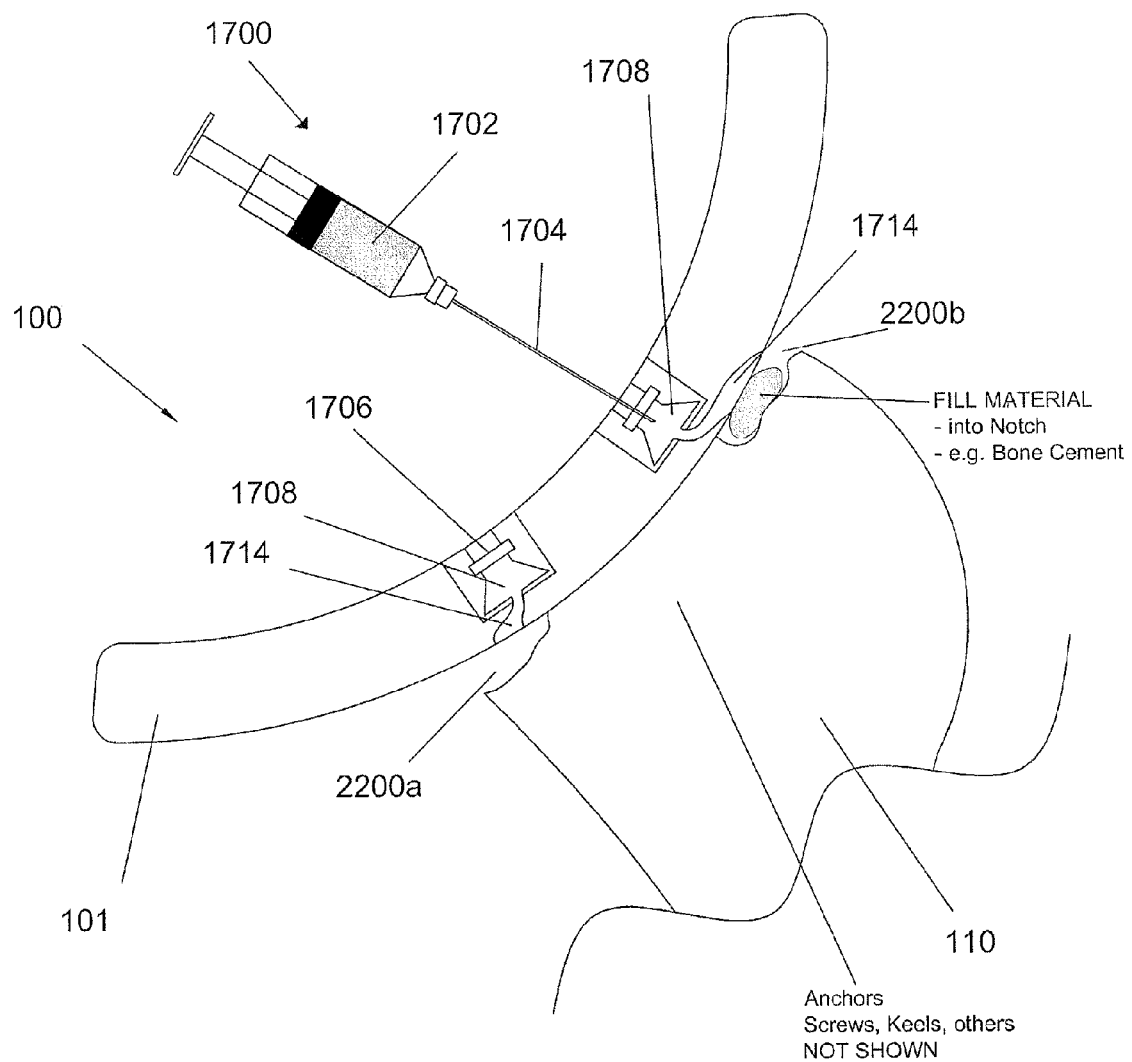
FIG. 30 is a top perspective view of an implantable shoulder prosthesis comprising a plurality of access ports through which an adhesive material can be added in accordance with embodiments of the present invention.

FIG. 30 is a top perspective view of an implantable shoulder prosthesis comprising a plurality of access ports through which an adhesive material can be added in accordance with embodiments of the present invention. A shoulder prosthesis 100 can comprise a glenoid member 101 having at least one access port or adhesive inlet disposed therein through which an adhesive material can be added.

The access port or adhesive inlet of the glenoid member 101 can comprise a resealable septum 1706, which can be connected inline with a chamber 1708 and an outlet port 1714.

After implantation of the glenoid member 101, a notch 2200a and/or 2200b can form in the glenoid region of a scapula 110 as a result of various types of load forces exerted on glenoid member 101. As a result of the notch 2200a and/or 2200b, loosening of the glenoid member 101 may occur, such as due to rocking. To prevent further damage to or loosening of the shoulder prosthesis 100 and surrounding glenoid area of the scapula 110, an adhesive or other fill material 1702, such as orthopedic bone cement or other fill material described above, can be injected via a syringe 1700 into notch 2200a and/or 2200b formed in the scapula 110.

In one embodiment, a needle 1704 of the syringe 1700 is used to pierce the resealable septum 1706. Once pierced, the adhesive material 1702 can be injected into the chamber 1708 and out of an output port 1714 into the notch 2200a and/or 2200b. As a result, loosening of the glenoid member 101 can be prevented.

One or more of the components described hereabove may be bioabsorbable or comprise a bioabsorbable portion, as has been described in reference to FIG. 20 hereabove. Bioabsorption of these portions is typically chosen to be at least one week, at least one month, at least three months, and at least six months. Single components or multiple components may be bioabsorbable, such as bioabsorbable portions which absorb at similar or dissimilar rates.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims.

We claim:

1. A method of securing an implantable shoulder prosthesis comprising:
    initially securing at least one fixation member of a glenoid member to a scapula of a patient, the glenoid member including a penetrable, re-sealable septum; and
    delivering injectable material via the septum into at least one transport tube of the glenoid member, wherein the delivering of the injectable material is performed at least twenty four hours after the initial securing of the at least one fixation member.

2. The method of claim 1 wherein the delivering of the injectable material causes the injectable material to exit at least one output port of the at least one fixation member.

3. The method of claim 1 wherein the glenoid member comprises an articulation surface and an opposing surface, and wherein the delivering of the injectable material causes the injectable material to exit at least one output port positioned on the opposing surface.

4. The method of claim 1 further comprising expanding the fixation member.

5. The method of claim 4 wherein the expanding of the fixation member is performed at least twenty four hours after the initial securing of the at least one fixation member.

6. A method of securing an implantable shoulder prosthesis comprising:
    initially securing at least one fixation member of a glenoid member to a scapula of a patient, the glenoid member including a penetrable, re-sealable septum; and
    delivering injectable material via the septum into at least one transport tube of the glenoid member; and
    expanding the fixation member, wherein the expanding of the fixation member is performed at least twenty four hours after the initial securing of the at least one fixation member.

7. The method of claim 6 wherein the delivering of the injectable material causes the injectable material to exit at least one output port of the at least one fixation member.

8. The method of claim 6 wherein the glenoid member comprises an articulation surface and an opposing surface, and wherein the delivering of the injectable material causes the injectable material to exit at least one output port positioned on the opposing surface.

\* \* \* \* \*